(12) United States Patent
Yanai et al.

(10) Patent No.: US 6,337,201 B1
(45) Date of Patent: Jan. 8, 2002

(54) β-FRUCTOFURANOSIDASE AND ITS GENE, METHOD OF ISOLATING β-FRUCTOFURANOSIDASE GENE, SYSTEM FOR PRODUCING β-FRUCTOFURANOSIDASE, AND β-FRUCTOFURANOSIDASE VARIANT

(75) Inventors: Koji Yanai; Akitaka Nakane; Hirofumi Nakamura; Yuko Baba; Akemi Watabe; Masao Hirayama, all of Sakado (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/142,623

(22) PCT Filed: Mar. 11, 1997

(86) PCT No.: PCT/JP97/00757

§ 371 Date: Sep. 10, 1998

§ 102(e) Date: Sep. 10, 1998

(87) PCT Pub. No.: WO97/34004

PCT Pub. Date: Sep. 18, 1997

(30) Foreign Application Priority Data

Mar. 11, 1996 (JP) ............................................. 8-053522
Jul. 26, 1996 (JP) ............................................. 8-197842

(51) Int. Cl.$^7$ .............................. C12N 9/24; C07K 14/00
(52) U.S. Cl. ........................ 435/200; 435/183; 435/193; 530/350
(58) Field of Search ................................ 435/183, 200, 435/193; 530/350

(56) References Cited

FOREIGN PATENT DOCUMENTS

JP          61268190          11/1986

OTHER PUBLICATIONS

Boddy et al. Purification and characterisation of an *Asperguillus niger* invertase and its DNA sequence, Curr. Genet. 24: 60–66, 1993.*

Y. Hatayama et al., "The purification of β–Fructofuranosidase from *Scopulariopsis brevicaulis* N–01", Nippon Nogeikagaku Kaishi, vol. 824 (70), p. 297 (1996).

Yoshiaki Hatakeyama et al., "Kinetic Parameters of β–Fructofuranosidase from *Scopulariopsis brevicaulis*", Journal of Fermentation and Bioengineering, vol. 81 (6), pp. 518–523 (1996).

Toyohiko Nakamura et al., "Occurrance of Two Forms of Extracellular Endoinulinase from *Aspergillus niger* Mutant 817", Journal of Fermentation and Bioengineering, vol. 78, No. 2, pp. 134–139 (1994).

L.M. Boddy et al., "Purification and Characterisation of an *Aspergillus niger* invertase and its DNA sequence", Current Genetics, vol. 24, pp. 60–66, (1993).

G. Blatch et al., "Molecular Characterization of a Fructanase Produced by *Bacteroides fragilis* BF–1", Journal of Bacteriology, vol. 175, No. 10, pp. 3058–3066, May 1993.

M. Hirayama et al. "Purification and Properties of a Fructooligosaccharide–producing β–Fructofuranosidase from *Aspergillus niger* ATCC 20611", Agricultural and Biological Chemistry, vol. 53, No. 3, pp. 667–673, (1989).

* cited by examiner

*Primary Examiner*—Rebecca E. Prouty
*Assistant Examiner*—Richard Hutson
(74) *Attorney, Agent, or Firm*—Wenderoth, Lind & Ponack, L.L.P.

(57) ABSTRACT

A novel β-fructofuranosidase gene and a β-fructofuranosidase encoded by the gene, a process for isolating a β-fructofuranosidase gene using the novel β-fructofuranosidase gene, and a novel β-fructofuranosidase obtained by this isolation process are disclosed. A novel mold fungus having no β-fructofuranosidase activity suitable for the production of β-fructofuranosidase, and a system for producing a recombinant β-fructofuranosidase using the novel mold fungus as a host is disclosed. Further, a β-fructofuranosidase variant which selectively and efficiently produces a specific fructooligosaccharide such as 1-kestose from sucrose is disclosed.

10 Claims, 10 Drawing Sheets

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
        (A) LENGTH: 635 amino acid residues
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Microorganism: Aspergillus niger ACE-2-1
        (ATCC 20611)

(ix) FEATURE:
        (A) NAME/KEY: mat peptide
        (B) LOCATION: 1..635
        (C) IDENTIFICATION METHOD: E (xi) SEQUENCE DESCRIPTION: SEQ ID NO:1:

```
Ser Tyr His Leu Asp Thr Thr Ala Pro Pro Thr Asn Leu Ser Thr
 1               5                  10                  15

Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
                35                  40                  45

Pro Ser Thr Gly Leu Phe His Val Gly Phe Leu His Asp Gly Asp Gly
        50                  55                  60

Ile Ala Gly Ala Thr Thr Ala Asn Leu Ala Thr Tyr Thr Asp Thr Ser
 65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
               100                 105                 110

Thr Leu Leu Tyr Thr Ser Val Ser Phe Leu Pro Ile His Trp Ser Ile
            115                 120                 125

Pro Tyr Thr Arg Gly Ser Glu Thr Gln Ser Leu Ala Val Ala Arg Asp
        130                 135                 140

Gly Gly Arg Arg Phe Asp Lys Leu Asp Gln Gly Pro Val Ile Ala Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Val Ala
                180                 185                 190

Arg Asn Glu Thr Ala Val Gln Gln Ala Val Asp Gly Trp Thr Glu Lys
            195                 200                 205
```

```
Asn Ala Pro Trp Tyr Val Ala Val Ser Gly Gly Val His Gly Val Gly
    210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Glu Gly Ser Gly Leu Pro
290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
                325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ser Ala Val Ser Lys Thr Ser Gly
        355                 360                 365

Val Glu Val Asp Arg Tyr Val Ser Phe Val Trp Leu Thr Gly Asp Gln
    370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Glu Gly Val Ser Trp Val Val Gly
            420                 425                 430

Glu Ser Asp Asn Gln Thr Ala Arg Leu Arg Thr Leu Gly Ile Thr Ile
        435                 440                 445

Ala Arg Glu Thr Lys Ala Ala Leu Leu Ala Asn Gly Ser Val Thr Ala
450                 455                 460

Glu Glu Asp Arg Thr Leu Gln Thr Ala Ala Val Val Pro Phe Ala Gln
465                 470                 475                 480

Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
            500                 505                 510

Ser Glu Leu Glu Arg Thr Ala Ile Tyr Tyr Gln Phe Ser Asn Glu Ser
        515                 520                 525

Leu Val Val Asp Arg Ser Gln Thr Ser Ala Ala Ala Pro Thr Asn Pro
530                 535                 540

Gly Leu Asp Ser Phe Thr Glu Ser Gly Lys Leu Arg Leu Phe Asp Val
545                 550                 555                 560

Ile Glu Asn Gly Gln Glu Gln Val Glu Thr Leu Asp Leu Thr Val Val
                565                 570                 575

Val Asp Asn Ala Val Val Glu Val Tyr Ala Asn Gly Arg Phe Ala Leu
            580                 585                 590

Ser Thr Trp Ala Arg Ser Trp Tyr Asp Asn Ser Thr Gln Ile Arg Phe
        595                 600                 605

Phe His Asn Gly Glu Gly Glu Val Gln Phe Arg Asn Val Ser Val Ser
    610                 615                 620

Glu Gly Leu Tyr Asn Ala Trp Pro Glu Arg Asn
```

625   630   635

(2) INFORMATION FOR SEQ ID NO:2:

(i) SEQUENCE CHARACTERISTICS:
        (A) LENGTH: 1905 base pairs
        (B) TYPE: Nucleic acid
        (C) STRANDEDNESS: Double stranded
        (D) TOPOLOGY: Linear (ii) MOLECULE TYPE: Genomic DNA (vi) ORIGINAL SOURCE:
        (A) ORGANISM: Microorganism: Aspergillus niger ACE-2-1
        (ATCC 20611)

(ix) FEATURE:
        (A) NAME/KEY: mat peptide
        (B) LOCATION: 1 .. 1905
        (C) IDENTIFICATION METHOD: E (xi) SEQUENCE DESCRIPTION: SEQ ID NO:2:

```
TCATACCACC TGGACACCAC GGCCCCGCCG CCGACCAACC TCAGCACCCT CCCCAACAAC      60
ACCCTCTTCC ACGTGTGGCG GCCGCGCGCG CACATCCTGC CCGCCGAGGG CCAGATCGGC     120
GACCCCTGCG CGCACTACAC CGACCCATCC ACCGGCCTCT TCCACGTGGG GTTCCTGCAC     180
GACGGGGACG GCATCGCGGG CGCCACCACG GCCAACCTGG CCACCTACAC CGATACCTCC     240
GATAACGGGA GCTTCCTGAT CCAGCCGGGC GGGAAGAACG ACCCCGTCGC CGTGTTCGAC     300
GGCGCCGTCA TCCCCGTCGG CGTCAACAAC ACCCCCACCT TACTCTACAC CTCCGTCTCC     360
TTCCTGCCCA TCCACTGGTC CATCCCCTAC ACCCGCGGCA GCGAGACGCA GTCGTTGGCC     420
GTCGCGCGCG ACGGCGGCCG CCGCTTCGAC AAGCTCGACC AGGGCCCCGT CATCGCCGAC     480
CACCCCTTCG CCGTCGACGT CACCGCCTTC CGCGATCCGT TTGTCTTCCG CAGTGCCAAG     540
TTGGATGTGC TGCTGTCGTT GGATGAGGAG GTGGCGCGGA ATGAGACGGC CGTGCAGCAG     600
GCCGTCGATG GCTGGACCGA GAAGAACGCC CCCTGGTATG TCGCGGTCTC TGGCGGGGTG     660
CACGGCGTCG GGCCCGCGCA GTTCCTCTAC CGCCAGAACG GCGGGAACGC TTCCGAGTTC     720
CAGTACTGGG AGTACCTCGG GGAGTGGTGG CAGGAGGCGA CCAACTCCAG CTGGGGCGAC     780
GAGGGCACCT GGGCCGGGCG CTGGGGGTTC AACTTGAGA CGGGGAATGT GCTCTTCCTC     840
ACCGAGGAGG CCATGACCCC CAGACGGGC GAGGTGTTCG TCACCCTCGG CACGGAGGGG     900
TCTGGCCTGC CAATCGTGCC GCAGGTCTCC AGTATCCACG ATATGCTGTG GCGGCGGGT     960
GAGGTCGGGG TGGGCAGTGA GCAGGAGGGT GCCAAGGTCG AGTTCTCCCC CTCCATGGCC    1020
GGGTTTCTGG ACTGGGGGTT CAGCGCCTAC GCTGCGGCGG GCAAGGTGCT GCCGGCCAGC    1080
TCGGCGGTGT CGAAGACCAG CGGCGTGGAG GTGGATCGGT ATGTCTCGTT CGTCTGGTTG    1140
ACGGGCGACC AGTACGAGCA GGCGGACGGG TTCCCCACGG CCCAGCAGGG GTGGACGGGG    1200
TCGCTGCTGC TGCCGCGCGA GCTGAAGGTG CAGACGGTGG AGAACGTCGT CGACAACGAG    1260
CTGGTGCGCG AGGAGGGCGT GTCGTGGGTG GTGGGGGAGT CGGACAACCA GACGGCCAGG    1320
CTGCGCACGC TGGGGATCAC GATCGCCCGG GAGACCAAGG CGGCCCTGCT GGCCAACGGC    1380
TCGGTGACCG CGGAGGAGGA CCGCACGCTG CAGACGGCGG CCGTCGTGCC GTTCGCGCAA    1440
TCGCCGAGCT CCAAGTTCTT CGTGCTGACG GCCCAGCTGG AGTTCCCCGC GAGCGCGCGC    1500
TCGTCCCCGC TCCAGTCCGG GTTCGAAATC CTGGCGTCGG AGCTGGAGCG CACGGCCATC    1560
TACTACCAGT TCAGCAACGA GTCGCTGGTC GTCGACCGCA GCCAGACTAG TGCGGCGGCG    1620
CCCACGAACC CCGGGCTGGA TAGCTTTACT GAGTCCGGCA AGTTGCGGTT GTTCGACGTG    1680
```

```
ATCGAGAACG GCCAGGAGCA GGTCGAGACG TTGGATCTCA CTGTCGTCGT GGATAACGCG    1740

GTTGTCGAGG TGTATGCCAA CGGGCGCTTT GCGTTGAGCA CCTGGGCGAG ATCGTGGTAC    1800

GACAACTCCA CCCAGATCCG CTTCTTCCAC AACGGCGAGG GCGAGGTGCA GTTCAGGAAT    1860

GTCTCCGTGT CGGAGGGGCT CTATAACGCC TGGCCGGAGA GAAAT                    1905

(2) INFORMATION FOR SEQ ID NO:3:

(i) SEQUENCE CHARACTERISTICS:
        (A) LENGTH: 20 amino acid residues
        (B) TYPE: Amino acid
        (C) STRANDEDNESS: Not Relevant
        (D) TOPOLOGY: Linear (ii) MOLECULE TYPE: Peptide (v) FRAGMENT TYPE: internal fragment (vi) ORIGINAL SOURCE:
        (A) ORGANISM: Microorganism: Aspergillus niger ACE-2-1
            (ATCC 20611)

(xi) SEQUENCE DESCRIPTION: SEQ ID NO:3:

Leu Asp Gln Gly Pro Val Ile Ala Asp His Pro Phe Ala Val Asp Val
 1               5                  10                  15

Thr Ala Phe Arg
            20

(2) INFORMATION FOR SEQ ID NO:4:

(i) SEQUENCE CHARACTERISTICS:
        (A) LENGTH: 20 amino acid residues
        (B) TYPE: Amino acid
        (C) STRANDEDNESS: Not Relevant
        (D) TOPOLOGY: Linear (ii) MOLECULE TYPE: Peptide (v) FRAGMENT TYPE: internal fragment (vi) ORIGINAL SOURCE:
        (A) ORGANISM: Microorganism: Aspergillus niger ACE-2-1
            (ATCC 20611)

(xi) SEQUENCE DESCRIPTION: SEQ ID NO:4:

Val Glu Phe Ser Pro Ser Met Ala Gly Phe Leu Asp Trp Gly Phe Ser
 1               5                  10                  15

Ala Tyr Ala Ala
            20

(2) INFORMATION FOR SEQ ID NO:5:

(i) SEQUENCE CHARACTERISTICS:
        (A) LENGTH: 20 amino acid residues
        (B) TYPE: Amino acid
        (C) STRANDEDNESS: Not Relevant
        (D) TOPOLOGY: Linear (ii) MOLECULE TYPE: Peptide (v) FRAGMENT TYPE: internal fragment (vi) ORIGINAL SOURCE:
        (A) ORGANISM: Microorganism: Aspergillus niger ACE-2-1
            (ATCC 20611)

(xi) SEQUENCE DESCRIPTION: SEQ ID NO:5:

Val Gln Thr Val Glu Asn Val Val Asp Asn Glu Leu Val Arg Glu Glu
```

```
    1               5              10              15
Gly Val Ser Trp
            20

(2) INFORMATION FOR SEQ ID NO:6:

(i) SEQUENCE CHARACTERISTICS:
        (A) LENGTH:  20 amino acid residues
        (B) TYPE:  Amino acid
        (C) STRANDEDNESS: Not Relevant
        (D) TOPOLOGY:  Linear (ii) MOLECULE TYPE:  Peptide (v) FRAGMENT TYPE:  internal fragment (vi) ORIGINAL SOURCE:
        (A) ORGANISM: Microorganism: Aspergillus niger ACE-2-1
        (ATCC 20611)

(xi) SEQUENCE DESCRIPTION: SEQ ID NO:6:

Ala Ala Leu Leu Ala Xaa Gly Ser Val Thr Ala Glu Glu Asp Arg Thr
 1               5                  10                  15
Leu Gln Thr Ala
            20

(2) INFORMATION FOR SEQ ID NO:7:

(i) SEQUENCE CHARACTERISTICS:
        (A) LENGTH:  6 amino acid residues
        (B) TYPE:  Amino acid
        (C) STRANDEDNESS: Not Relevant
        (D) TOPOLOGY:  Linear (ii) MOLECULE TYPE:  Peptide (v) FRAGMENT TYPE:  N-terminal fragment (vi) ORIGINAL SOURCE:
        (A) ORGANISM: Microorganism: Aspergillus niger ACE-2-1
        (ATCC 20611)

(xi) SEQUENCE DESCRIPTION: SEQ ID NO:7:

Ser Tyr His Leu Asp Thr
 1               5

(2) INFORMATION FOR SEQ ID NO:8:

(i) SEQUENCE CHARACTERISTICS:
        (A) LENGTH:  20 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:8:

ATCGCSGAYC AYCCSTTYGC                                              20

(2) INFORMATION FOR SEQ ID NO:9:

(i) SEQUENCE CHARACTERISTICS:
        (A) LENGTH:  20 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:9:
```

TCRTTRTCSA CSACRTTYTC                                              20

(2) INFORMATION FOR SEQ ID NO:10:

(i) SEQUENCE CHARACTERISTICS:
        (A) LENGTH: 788 base pairs
        (B) TYPE: Nucleic acid
        (C) STRANDEDNESS: Double stranded
        (D) TOPOLOGY: Linear (vi) ORIGINAL SOURCE:
        (A) ORGANISM: Microorganism: Aspergillus niger ACE-2-1
            (ATCC 20611)

(ix) FEATURE:
        (A) NAME/KEY: P CDS(partial amino acid sequence)
        (B) LOCATION: 1 .. 788
        (C) IDENTIFICATION METHOD: E (xi) SEQUENCE DESCRIPTION: SEQ ID NO:10:

```
ATC GCC GAC CAC CCC TTC GCC GTC GAC GTC ACC GCC TTC CGC GAT CCG     48
Ile Ala Asp His Pro Phe Ala Val Asp Val Thr Ala Phe Arg Asp Pro
 1               5                  10                  15

TTT GTC TTC CGC AGT GCC AAG TTG GAT GTG CTG CTG TCG TTG GAT GAG     96
Phe Val Phe Arg Ser Ala Lys Leu Asp Val Leu Leu Ser Leu Asp Glu
             20                  25                  30

GAG GTG GCG CGG AAT GAG ACG GCC GTG CAG CAG GCC GTC GAT GGC TGG    144
Glu Val Ala Arg Asn Glu Thr Ala Val Gln Gln Ala Val Asp Gly Trp
         35                  40                  45

ACC GAG AAG AAC GCC CCC TGG TAT GTC GCG GTC TCT GGC GGG GTG CAC    192
Thr Glu Lys Asn Ala Pro Trp Tyr Val Ala Val Ser Gly Gly Val His
     50                  55                  60

GGC GTC GGG CCC GCG CAG TTC CTC TAC CGC CAG AAC GGC GGG AAC GCT    240
Gly Val Gly Pro Ala Gln Phe Leu Tyr Arg Gln Asn Gly Gly Asn Ala
 65                  70                  75                  80

TCC GAG TTC CAG TAC TGG GAG TAC CTC GGG GAG TGG TGG CAG GAG GCG    288
Ser Glu Phe Gln Tyr Trp Glu Tyr Leu Gly Glu Trp Trp Gln Glu Ala
                 85                  90                  95

ACC AAC TCC AGC TGG GGC GAC GAG GGC ACC TGG GCC GGG CGC TGG GGG    336
Thr Asn Ser Ser Trp Gly Asp Glu Gly Thr Trp Ala Gly Arg Trp Gly
            100                 105                 110

TTC AAC TTC GAG ACG GGG AAT GTG CTC TTC CTC ACC GAG GAG GGC CAT    384
Phe Asn Phe Glu Thr Gly Asn Val Leu Phe Leu Thr Glu Glu Gly His
        115                 120                 125

GAC CCC CAG ACG GGC GAG GTG TTC GTC ACC CTC GGC ACG GAG GGG TCT    432
Asp Pro Gln Thr Gly Glu Val Phe Val Thr Leu Gly Thr Glu Gly Ser
    130                 135                 140

GGC CTG CCA ATC GTG CCG CAG GTC TCC AGT ATC CAC GAT ATG CTG TGG    480
Gly Leu Pro Ile Val Pro Gln Val Ser Ser Ile His Asp Met Leu Trp
145                 150                 155                 160

GCG GCG GGT GAG GTC GGG GTG GGC AGT GAG CAG GAG GGT GCC AAG GTC    528
Ala Ala Gly Glu Val Gly Val Gly Ser Glu Gln Glu Gly Ala Lys Val
                165                 170                 175

GAG TTC TCC CCC TCC ATG GCC GGG TTT CTG GAC TGG GGG TTC AGC GCC    576
Glu Phe Ser Pro Ser Met Ala Gly Phe Leu Asp Trp Gly Phe Ser Ala
            180                 185                 190

TAC GCT GCG GCG GGC AAG GTG CTG CCG GCC AGC TCG GCG GTG TCG AAG    624
Tyr Ala Ala Ala Gly Lys Val Leu Pro Ala Ser Ser Ala Val Ser Lys
        195                 200                 205

ACC AGC GGC GTG GAG GTG GAT CGG TAT GTC TCG TTC GTC TGG TTG ACG    672
Thr Ser Gly Val Glu Val Asp Arg Tyr Val Ser Phe Val Trp Leu Thr
    210                 215                 220
```

-continued

```
GGC GAC CAG TAC GAG CAG GCG GAC GGG TTC CCC ACG GCC CAG CAG GGG      720
Gly Asp Gln Tyr Glu Gln Ala Asp Gly Phe Pro Thr Ala Gln Gln Gly
225                 230                 235                 240

TGG ACG GGG TCG CTG CTG CTG CCG CGC GAG CTG AAG GTG CAG ACG GTG      768
Trp Thr Gly Ser Leu Leu Leu Pro Arg Glu Leu Lys Val Gln Thr Val
                245                 250                 255

GAG AAC GTC GTC GAC AAC GA                                           788
Glu Asn Val Val Asp Asn
            260
```

(2) INFORMATION FOR SEQ ID NO:11:

(i) SEQUENCE CHARACTERISTICS:
    (A) LENGTH: 565 amino acid residues
    (B) TYPE: Amino acid
    (C) STRANDEDNESS: Not Relevant
    (D) TOPOLOGY: Not Relevant (ii) MOLECULE TYPE: protein (vi) ORIGINAL SOURCE:
    (A) ORGANISM: Microorganism: Penicillium roqueforti IAM7254

(ix) FEATURE:
    (A) NAME/KEY: mat peptide
    (B) LOCATION: 1 .. 565
    (C) IDENTIFICATION METHOD: E (xi) SEQUENCE DESCRIPTION: SEQ ID NO:11:

```
Val Asp Phe His Thr Pro Ile Asp Tyr Asn Ser Ala Pro Pro Asn Leu
1               5                   10                  15

Ser Thr Leu Ala Asn Ala Ser Leu Phe Lys Thr Trp Arg Pro Arg Ala
                20                  25                  30

His Leu Leu Pro Pro Ser Gly Asn Ile Gly Asp Pro Cys Gly His Tyr
                35                  40                  45

Thr Asp Pro Lys Thr Gly Leu Phe His Val Gly Trp Leu Tyr Ser Gly
            50                  55                  60

Ile Ser Gly Ala Thr Thr Asp Asp Leu Val Thr Tyr Lys Asp Leu Asn
65                  70                  75                  80

Pro Asp Gly Ala Pro Ser Ile Val Ala Gly Lys Asn Asp Pro Leu
                85                  90                  95

Ser Val Phe Asp Gly Ser Val Ile Pro Ser Gly Ile Asp Gly Met Pro
                100                 105                 110

Thr Leu Leu Tyr Thr Ser Val Ser Tyr Leu Pro Ile His Trp Ser Ile
                115                 120                 125

Pro Tyr Thr Arg Gly Ser Glu Thr Gln Ser Leu Ala Val Ser Tyr Asp
                130                 135                 140

Gly Gly His Asn Phe Thr Lys Leu Asn Gln Gly Pro Val Ile Pro Thr
145                 150                 155                 160

Pro Pro Phe Ala Leu Asn Val Thr Ala Phe Arg Asp Pro Tyr Val Phe
                165                 170                 175

Gln Ser Pro Ile Leu Asp Lys Ser Val Asn Ser Thr Gln Gly Thr Trp
                180                 185                 190

Tyr Val Ala Ile Ser Gly Gly Val His Gly Val Gly Pro Cys Gln Phe
                195                 200                 205

Leu Tyr Arg Gln Asn Asp Ala Asp Phe Gln Tyr Trp Glu Tyr Leu Gly
                210                 215                 220

Gln Trp Trp Lys Glu Pro Leu Asn Thr Thr Trp Gly Lys Gly Asp Trp
225                 230                 235                 240

Ala Gly Gly Trp Gly Phe Asn Phe Glu Val Gly Asn Val Phe Ser Leu
```

```
                    245                 250                 255
Asn Ala Glu Gly Tyr Ser Asp Gly Glu Ile Phe Ile Thr Leu Gly
                260                 265                 270

Ala Glu Gly Ser Gly Leu Pro Ile Val Pro Gln Val Ser Ser Ile Arg
            275                 280                 285

Asp Met Leu Trp Val Thr Gly Asn Val Thr Asn Asp Gly Ser Val Thr
    290                 295                 300

Phe Lys Pro Thr Met Ala Gly Val Leu Asp Trp Gly Val Ser Ala Tyr
305                 310                 315                 320

Ala Ala Ala Gly Lys Ile Leu Pro Ala Ser Gln Ala Ser Thr Lys
                325                 330                 335

Ser Gly Ala Pro Asp Arg Phe Ile Ser Tyr Val Trp Leu Thr Gly Asp
            340                 345                 350

Leu Phe Glu Gln Val Lys Gly Phe Pro Thr Ala Gln Gln Asn Trp Thr
                355                 360                 365

Gly Ala Leu Leu Leu Pro Arg Glu Leu Asn Val Arg Thr Ile Ser Asn
    370                 375                 380

Val Val Asp Asn Glu Leu Ser Arg Glu Ser Leu Thr Ser Trp Arg Val
385                 390                 395                 400

Ala Arg Glu Asp Ser Gly Gln Ile Asp Leu Glu Thr Met Gly Ile Ser
                405                 410                 415

Ile Ser Arg Glu Thr Tyr Ser Ala Leu Thr Ser Gly Ser Ser Phe Val
            420                 425                 430

Glu Ser Gly Lys Thr Leu Ser Asn Ala Gly Ala Val Pro Phe Asn Thr
                435                 440                 445

Ser Pro Ser Ser Lys Phe Phe Val Leu Thr Ala Asn Ile Ser Phe Pro
    450                 455                 460

Thr Ser Ala Arg Asp Ser Gly Ile Gln Ala Gly Phe Gln Val Leu Ser
465                 470                 475                 480

Ser Ser Leu Glu Ser Thr Thr Ile Tyr Tyr Gln Phe Ser Asn Glu Ser
                485                 490                 495

Ile Ile Val Asp Arg Ser Asn Thr Ser Ala Ala Ala Arg Thr Thr Ala
            500                 505                 510

Gly Ile Leu Ser Asp Asn Glu Ala Gly Arg Leu Arg Leu Phe Asp Val
        515                 520                 525

Leu Arg Asn Gly Lys Glu Gln Val Glu Thr Leu Glu Leu Thr Ile Val
    530                 535                 540

Val Asp Asn Ser Val Leu Glu Val Tyr Ala Asn Gly Arg Phe Ala Leu
545                 550                 555                 560

Gly Thr Trp Ala Arg
                565

(2) INFORMATION FOR SEQ ID NO:12:

(i) SEQUENCE CHARACTERISTICS:
        (A) LENGTH: 1695 base pairs
        (B) TYPE: Nucleic acid
        (C) STRANDEDNESS: Double stranded
        (D) TOPOLOGY: Linear (ii) MOLECULE TYPE: Genomic DNA (vi) ORIGINAL SOURCE:
         (A) ORGANISM: Microorganism: Penicillium roqueforti IAM7254

(ix) FEATURE:
         (A) NAME/KEY: mat peptide
         (B) LOCATION: 1 .. 1695
```

(C) IDENTIFICATION METHOD: E (xi) SEQUENCE DESCRIPTION: SEQ ID NO:12:

| | | | | | |
|---|---|---|---|---|---|
| GTTGATTTCC | ATACCCCGAT | TGACTATAAC | TCGGCTCCGC | CAAACCTTTC | TACCCTGGCA | 60 |
| AACGCATCTC | TTTTCAAGAC | ATGGAGACCC | AGAGCCCATC | TTCTCCCTCC | ATCTGGGAAC | 120 |
| ATAGGCGACC | CGTGCGGGCA | CTATACCGAT | CCCAAGACTG | GTCTCTTCCA | CGTGGGTTGG | 180 |
| CTTTACAGTG | GGATTTCGGG | AGCGACAACC | GACGATCTCG | TTACCTATAA | AGACCTCAAT | 240 |
| CCCGATGGAG | CCCCGTCAAT | TGTTGCAGGA | GGAAAGAACG | ACCCTCTTTC | TGTCTTCGAT | 300 |
| GGCTCGGTCA | TTCCAAGCGG | TATAGACGGC | ATGCCAACTC | TTCTGTATAC | CTCTGTATCA | 360 |
| TACCTCCCAA | TCCACTGGTC | CATCCCCTAC | ACCCGGGGAA | GCGAGACACA | ATCCTTGGCC | 420 |
| GTTTCCTATG | ACGGTGGTCA | CAACTTCACC | AAGCTCAACC | AAGGGCCCGT | GATCCCTACG | 480 |
| CCTCCGTTTG | CTCTCAATGT | CACCGCTTTC | CGTGACCCCT | ACGTTTTCCA | AAGCCCAATT | 540 |
| CTGGACAAAT | CTGTCAATAG | TACCCAAGGA | ACATGGTATG | TCGCCATATC | TGGCGGTGTC | 600 |
| CACGGTGTCG | GACCTTGTCA | GTTCCTCTAC | CGTCAGAACG | ACGCAGATTT | TCAATATTGG | 660 |
| GAATATCTCG | GGCAATGGTG | GAAGGAGCCC | CTTAATACCA | CTTGGGGAAA | GGGTGACTGG | 720 |
| GCCGGGGGTT | GGGGCTTCAA | CTTTGAGGTT | GGCAACGTCT | TTAGTCTGAA | TGCAGAGGGG | 780 |
| TATAGTGAAG | ACGGCGAGAT | ATTCATAACC | CTCGGTGCTG | AGGGTTCGGG | ACTTCCCATC | 840 |
| GTTCCTCAAG | TCTCCTCTAT | TCGCGATATG | CTGTGGGTGA | CCGGCAATGT | CACAAATGAC | 900 |
| GGCTCTGTCA | CTTTCAAGCC | AACCATGGCG | GGTGTGCTTG | ACTGGGCGT | GTCGGCATAT | 960 |
| GCTGCTGCAG | GCAAGATCTT | GCCGGCCAGC | TCTCAGGCAT | CCACAAAGAG | CGGTGCCCCC | 1020 |
| GATCGGTTCA | TTTCCTATGT | CTGGCTCACT | GGAGATCTAT | TCGAGCAAGT | GAAAGGATTC | 1080 |
| CCTACCGCTC | AACAAAACTG | GACCGGGGCC | CTCTTACTGC | CGCGAGAGCT | GAATGTCCGC | 1140 |
| ACTATCTCTA | ACGTGGTGGA | TAACGAACTT | TCGCGTGAGT | CCTTGACATC | GTGGCGCGTG | 1200 |
| GCCCGCGAAG | ACTCTGGTCA | GATCGACCTT | GAAACAATGG | GAATCTCAAT | TTCCAGGGAG | 1260 |
| ACTTACAGCG | CTCTCACATC | CGGCTCATCT | TTTGTCGAGT | CTGGTAAAAC | GTTGTCGAAT | 1320 |
| GCTGGAGCAG | TGCCCTTCAA | TACCTCACCC | TCAAGCAAGT | TCTTCGTGCT | GACAGCAAAT | 1380 |
| ATATCTTTCC | CGACCTCTGC | CCGTGACTCT | GGCATCCAGG | CTGGTTTCCA | GGTTTTATCC | 1440 |
| TCTAGTCTTG | AGTCTACAAC | TATCTACTAC | CAATTCTCCA | ACGAGTCCAT | CATCGTCGAC | 1500 |
| CGCAGCAACA | CGAGTGCTGC | GGCGAGAACA | ACTGCTGGGA | TCCTCAGTGA | TAACGAGGCG | 1560 |
| GGACGTCTGC | GCCTCTTCGA | CGTGTTGCGA | AATGGAAAAG | AACAGGTTGA | AACTTTGGAG | 1620 |
| CTCACTATCG | TGGTGGATAA | TAGTGTACTG | GAAGTATATG | CCAATGGACG | CTTTGCTCTA | 1680 |
| GGCACTTGGG | CTCGG | | | | | 1695 |

(2) INFORMATION FOR SEQ ID NO:13:

(i) SEQUENCE CHARACTERISTICS:
        (A) LENGTH: 574 amino acid residues
        (B) TYPE: Amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Microorganism: Scopulariopsis brevicaulis IFO4843

(ix) FEATURE:
        (A) NAME/KEY: mat peptide (B) LOCATION: 1 .. 574
(C) IDENTIFICATION METHOD: E (xi) SEQUENCE DESCRIPTION: SEQ ID NO:13:

```
Gln Pro Thr Ser Leu Ser Ile Asp Asn Ser Thr Tyr Pro Ser Ile Asp
 1               5                  10                  15
Tyr Asn Ser Ala Pro Pro Asn Leu Ser Thr Leu Ala Asn Asn Ser Leu
            20                  25                  30
Phe Glu Thr Trp Arg Pro Arg Ala His Val Leu Pro Pro Gln Asn Gln
        35                  40                  45
Ile Gly Asp Pro Cys Met His Tyr Thr Asp Pro Glu Thr Gly Ile Phe
 50                  55                  60
His Val Gly Trp Leu Tyr Asn Gly Asn Gly Ala Ser Gly Ala Thr Thr
 65                  70                  75                  80
Glu Asp Leu Val Thr Tyr Gln Asp Leu Asn Pro Asp Gly Ala Gln Met
                85                  90                  95
Ile Leu Pro Gly Gly Val Asn Asp Pro Ile Ala Val Phe Asp Gly Ala
            100                 105                 110
Val Ile Pro Ser Gly Ile Asp Gly Lys Pro Thr Met Met Tyr Thr Ser
        115                 120                 125
Val Ser Tyr Met Pro Ile Ser Trp Ser Ile Ala Tyr Thr Arg Gly Ser
130                 135                 140
Glu Thr His Ser Leu Ala Val Ser Ser Asp Gly Gly Lys Asn Phe Thr
145                 150                 155                 160
Lys Leu Val Gln Gly Pro Val Ile Pro Ser Pro Phe Gly Ala Asn
                165                 170                 175
Val Thr Ser Trp Arg Asp Pro Phe Leu Phe Gln Asn Pro Gln Phe Asp
            180                 185                 190
Ser Leu Leu Glu Ser Glu Asn Gly Thr Trp Tyr Thr Val Ile Ser Gly
        195                 200                 205
Gly Ile His Gly Asp Gly Pro Ser Ala Phe Leu Tyr Arg Gln His Asp
210                 215                 220
Pro Asp Phe Gln Tyr Trp Glu Tyr Leu Gly Pro Trp Trp Asn Glu Glu
225                 230                 235                 240
Gly Asn Ser Thr Trp Gly Ser Gly Asp Trp Ala Gly Arg Trp Gly Tyr
                245                 250                 255
Asn Phe Glu Val Ile Asn Ile Val Gly Leu Asp Asp Asp Gly Tyr Asn
            260                 265                 270
Pro Asp Gly Glu Ile Phe Ala Thr Val Gly Thr Glu Trp Ser Phe Asp
        275                 280                 285
Pro Ile Lys Pro Gln Ala Ser Asp Asn Arg Glu Met Leu Trp Ala Ala
290                 295                 300
Gly Asn Met Thr Leu Glu Asp Gly Asp Ile Lys Phe Thr Pro Ser Met
305                 310                 315                 320
Ala Gly Tyr Leu Asp Trp Gly Leu Ser Ala Tyr Ala Ala Gly Lys
                325                 330                 335
Glu Leu Pro Ala Ser Ser Lys Pro Ser Gln Lys Ser Gly Ala Pro Asp
            340                 345                 350
Arg Phe Val Ser Tyr Leu Trp Leu Thr Gly Asp Tyr Phe Glu Gly His
        355                 360                 365
Asp Phe Pro Thr Pro Gln Gln Asn Trp Thr Gly Ser Leu Leu Leu Pro
370                 375                 380
Arg Glu Leu Ser Val Gly Thr Ile Pro Asn Val Val Asp Asn Glu Leu
385                 390                 395                 400
```

```
Ala Arg Glu Thr Gly Ser Trp Arg Val Gly Thr Asn Asp Thr Gly Val
            405                 410                 415

Leu Glu Leu Val Thr Leu Lys Gln Glu Ile Ala Arg Glu Thr Leu Ala
            420                 425                 430

Glu Met Thr Ser Gly Asn Ser Phe Thr Glu Ala Ser Arg Asn Val Ser
            435                 440                 445

Ser Pro Gly Ser Thr Ala Phe Gln Gln Ser Leu Asp Ser Lys Phe Phe
            450                 455                 460

Val Leu Thr Ala Ser Leu Ser Phe Pro Ser Ser Ala Arg Asp Ser Asp
465                 470                 475                 480

Leu Lys Ala Gly Phe Glu Ile Leu Ser Ser Glu Phe Glu Ser Thr Thr
            485                 490                 495

Val Tyr Tyr Gln Phe Ser Asn Glu Ser Ile Ile Ile Asp Arg Ser Asn
            500                 505                 510

Ser Ser Ala Ala Ala Leu Thr Thr Asp Gly Ile Asp Thr Arg Asn Glu
            515                 520                 525

Phe Gly Lys Met Arg Leu Phe Asp Val Val Glu Gly Asp Gln Glu Arg
            530                 535                 540

Ile Glu Thr Leu Asp Leu Thr Ile Val Val Asp Asn Ser Ile Val Glu
545                 550                 555                 560

Val His Ala Asn Gly Arg Phe Ala Leu Ser Thr Trp Val Arg
            565                 570
```

(2) INFORMATION FOR SEQ ID NO:14:

(i) SEQUENCE CHARACTERISTICS:
        (A) LENGTH: 1722 base pairs
        (B) TYPE: Nucleic acid
        (C) STRANDEDNESS: Double stranded
        (D) TOPOLOGY: Linear (ii) MOLECULE TYPE: Genomic DNA (vi) ORIGINAL SOURCE:
        (A) ORGANISM: Microorganism: Scopulariopsis brevicaulis
            IFO4843

(ix) FEATURE:
        (A) NAME/KEY: mat peptide
        (B) LOCATION: 1 .. 1722
        (C) IDENTIFICATION METHOD: E (xi) SEQUENCE DESCRIPTION: SEQ ID NO:14:

```
CAACCTACGT CTCTGTCAAT CGACAATTCC ACGTATCCTT CTATCGACTA CAACTCCGCC      60

CCTCCAAACC TCTCGACTCT TGCCAACAAC AGCCTCTTCG AGACATGGAG GCCGAGGGCA     120

CACGTCCTTC CGCCCCAGAA CCAGATCGGC GATCCGTGTA TGCACTACAC CGACCCCGAG     180

ACAGGAATCT TCCACGTCGG CTGGCTGTAC AACGGCAATG GCGCTTCCGG CGCCACGACC     240

GAGGATCTCG TCACCTATCA GGATCTCAAC CCCGACGGAG CGCAGATGAT CCTTCCGGGT     300

GGTGTGAATG ACCCCATTGC TGTCTTTGAC GGCGCGGTTA TTCCCAGTGG CATTGATGGG     360

AAACCCACCA TGATGTATAC CTCGGTGTCA TACATGCCCA TCTCCTGGAG CATCGCTTAC     420

ACCAGGGGAA GCGAGACCCA CTCTCTCGCA GTGTCGTCCG ACGGCGGTAA GAACTTCACC     480

AAGCTGGTGC AGGGCCCCGT CATTCCTTCG CCTCCCTTCG GCGCCAACGT GACCAGCTGG     540

CGTGACCCCT TCCTGTTCCA AAACCCCCAG TTCGACTCTC TCCTCGAAAG CGAGAACGGC     600

ACGTGGTACA CCGTTATCTC TGGTGGCATC CACGGTGACG GCCCCTCCGC GTTCCTCTAC     660

CGTCAGCACG ACCCCGACTT CCAGTACTGG GAGTACCTTG ACCGTGGTGT GAACGAGGAA     720
```

```
GGGAACTCGA CCTGGGGCAG CGGTGACTGG GCTGGCCGGT GGGGCTACAA CTTCGAGGTC      780

ATCAACATTG TCGGTCTTGA CGATGATGGC TACAACCCCG ACGGTGAAAT CTTTGCCACG      840

GTAGGTACCG AATGGTCGTT TGACCCCATC AAACCGCAGG CCTCGGACAA CAGGGAGATG      900

CTCTGGGCCG CGGGCAACAT GACTCTCGAG GACGGCGATA TCAAGTTCAC GCCAAGCATG      960

GCGGGCTACC TCGACTGGGG TCTATCGGCG TATGCCGCCG CTGGCAAGGA GCTGCCCGCT     1020

TCTTCAAAGC CTTCGCAGAA GAGCGGTGCG CCGGACCGGT TCGTGTCGTA CCTGTGGCTC     1080

ACCGGTGACT ACTTCGAGGG CCACGACTTC CCCACCCCGC AGCAGAATTG GACCGGCTCG     1140

CTTTTGCTTC CGCGTGAGCT GAGCGTCGGG ACGATTCCCA ACGTTGTCGA CAACGAGCTT     1200

GCTCGCGAGA CGGGCTCTTG GAGGGTTGGC ACCAACGACA CTGGCGTGCT TGAGCTGGTC     1260

ACTCTGAAGC AGGAGATTGC TCGCGAGACG CTGGCTGAAA TGACCAGCGG CAACTCCTTC     1320

ACCGAGGCGA GCAGGAATGT CAGCTCGCCC GGATCTACCG CCTTCCAGCA GTCCCTGGAT     1380

TCCAAGTTCT TCGTCCTGAC CGCCTCGCTC TCCTTCCCTT CGTCGGCTCG CGACTCCGAC     1440

CTCAAGGCTG GTTTCGAGAT CCTGTCGTCC GAGTTTGAGT CGACCACGGT CTACTACCAG     1500

TTTTCCAACG AGTCCATCAT CATTGACCGG AGCAACTCGA GTGCTGCCGC CTTGACTACC     1560

GATGGAATCA CACCCGCAA CGAGTTTGGC AAGATGCGCC TGTTTGATGT TGTCGAGGGT     1620

GACCAGGAGC GTATCGAGAC GCTCGATCTC ACTATTGTGG TTGATAACTC GATCGTTGAG     1680

GTTCATGCCA ACGGGCGATT CGCTCTGAGC ACTTGGGTTC GG                        1722

(2) INFORMATION FOR SEQ ID NO:15:

(i) SEQUENCE CHARACTERISTICS:
        (A) LENGTH:  28 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:15:

GCGAATTCCA ATGAAGCTCA CCACTACC                                        28

(2) INFORMATION FOR SEQ ID NO:16:

(i) SEQUENCE CHARACTERISTICS:
        (A) LENGTH:  24 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:16:

GCGGATCCCG GTCAATTTCT CTCC                                            24

(2) INFORMATION FOR SEQ ID NO:17:

(i) SEQUENCE CHARACTERISTICS:
        (A) LENGTH:  19 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:17:

GACTGACCGG TGTTCATCC                                                  19
```

(2) INFORMATION FOR SEQ ID NO:18:

(i) SEQUENCE CHARACTERISTICS:
        (A) LENGTH:  20 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:18:

CTCGGTTGTC ATAGATGTGG                                              20

(2) INFORMATION FOR SEQ ID NO:19:

(i) SEQUENCE CHARACTERISTICS:
        (A) LENGTH:  24 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:19:

CAATCCAGGA GGATCCCAAT GAAG                                        24

(2) INFORMATION FOR SEQ ID NO:20:

(i) SEQUENCE CHARACTERISTICS:
        (A) LENGTH:  22 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:20:

TGACCGGGAT CCGGGCATGC AG                                          22

(2) INFORMATION FOR SEQ ID NO:21:

(i) SEQUENCE CHARACTERISTICS:
        (A) LENGTH:  24 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:21:

CGCGTCGTCT AGAGGTTGTC ACTT                                        24

(2) INFORMATION FOR SEQ ID NO:22:

(i) SEQUENCE CHARACTERISTICS:
        (A) LENGTH:  21 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:22:

CCCTATTGGG GTCCATGGCC C                                            21

(2) INFORMATION FOR SEQ ID NO:23:

(i) SEQUENCE CHARACTERISTICS:
    (A) LENGTH: 22 base pairs
    (B) TYPE: Nucleic acid
    (C) STRANDEDNESS: Not Relevant
    (D) TOPOLOGY: Linear (ii) MOLECULE TYPE: Synthetic DNA (xi) SEQUENCE DESCRIPTION: SEQ ID NO:23:

CAACTGCTGG CATCCTCAGT GA                                                22

(2) INFORMATION FOR SEQ ID NO:24:

(i) SEQUENCE CHARACTERISTICS:
        (A) LENGTH: 30 base pairs
        (B) TYPE: Nucleic acid
        (C) STRANDEDNESS: Not Relevant
        (D) TOPOLOGY: Linear (ii) MOLECULE TYPE: Synthetic DNA (xi) SEQUENCE DESCRIPTION: SEQ ID NO:24:

GCGGATCCAT GAAGCTATCA AATGCAATCA                                        30

(2) INFORMATION FOR SEQ ID NO:25:

(i) SEQUENCE CHARACTERISTICS:
        (A) LENGTH: 26 base pairs
        (B) TYPE: Nucleic acid
        (C) STRANDEDNESS: Not Relevant
        (D) TOPOLOGY: Linear (ii) MOLECULE TYPE: Synthetic DNA (xi) SEQUENCE DESCRIPTION: SEQ ID NO:25:

GCGGATCCTT ACCGAGCCCA AGTGCC                                            26

(2) INFORMATION FOR SEQ ID NO:26:

(i) SEQUENCE CHARACTERISTICS:
        (A) LENGTH: 27 base pairs
        (B) TYPE: Nucleic acid
        (C) STRANDEDNESS: Not Relevant
        (D) TOPOLOGY: Linear (ii) MOLECULE TYPE: Synthetic DNA (xi) SEQUENCE DESCRIPTION: SEQ ID NO:26:

GCGGATCCAA TGAAGCTCAC CACTACC                                           27

(2) INFORMATION FOR SEQ ID NO:27:

(i) SEQUENCE CHARACTERISTICS:
        (A) LENGTH: 24 base pairs
        (B) TYPE: Nucleic acid
        (C) STRANDEDNESS: Not Relevant
        (D) TOPOLOGY: Linear (ii) MOLECULE TYPE: Synthetic DNA (xi) SEQUENCE DESCRIPTION: SEQ ID NO:27:

GCGGATCCCG GTCAATTTCT CTCC                                              24

(2) INFORMATION FOR SEQ ID NO:28:

(i) SEQUENCE CHARACTERISTICS:
        (A) LENGTH: 21 base pairs
        (B) TYPE: Nucleic acid
        (C) STRANDEDNESS: Not Relevant (D) TOPOLOGY:  Linear (ii) MOLECULE TYPE:  Synthetic DNA (xi) SEQUENCE DESCRIPTION: SEQ ID NO:28:

GTCACCGCCT GGCGCGATCC G                                              21

(2) INFORMATION FOR SEQ ID NO:29:

(i) SEQUENCE CHARACTERISTICS:
        (A) LENGTH:   19 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:29:

GGCACGGAGT GGTCTGGCC                                                 19

(2) INFORMATION FOR SEQ ID NO:30:

(i) SEQUENCE CHARACTERISTICS:
        (A) LENGTH:   24 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:30:

CTCCAGTATC AAGGATATGC TGTG                                           24

(2) INFORMATION FOR SEQ ID NO:31:

(i) SEQUENCE CHARACTERISTICS:
        (A) LENGTH:   20 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:31:

CGACCAGTAC AAGCAGGCGG                                                20

(2) INFORMATION FOR SEQ ID NO:32:

(i) SEQUENCE CHARACTERISTICS:
        (A) LENGTH:   21 base pairs
        (B) TYPE:  Nucleic acid
        (C) STRANDEDNESS: Not Relevant
        (D) TOPOLOGY:  Linear (ii) MOLECULE TYPE:  Synthetic DNA (xi) SEQUENCE DESCRIPTION: SEQ ID NO:32:

TCCAGTATCC GCGATATGCT G                                              21

(2) INFORMATION FOR SEQ ID NO:33:

(i) SEQUENCE CHARACTERISTICS:
        (A) LENGTH:   23 base pairs
        (B) TYPE:  Nucleic acid
        (C) STRANDEDNESS: Not Relevant
        (D) TOPOLOGY:  Linear (ii) MOLECULE TYPE:  Synthetic DNA -continued (xi) SEQUENCE DESCRIPTION: SEQ ID NO:33:

CGGCACGGAG GTTTCTGGCC TGC                                                23

(2) INFORMATION FOR SEQ ID NO:34:

(i) SEQUENCE CHARACTERISTICS:
        (A) LENGTH: 23 base pairs
        (B) TYPE: Nucleic acid
        (C) STRANDEDNESS: Not Relevant
        (D) TOPOLOGY: Linear (ii) MOLECULE TYPE: Synthetic DNA (xi) SEQUENCE DESCRIPTION: SEQ ID NO:34:

CGGCACGGAG GAGTCTGGCC TGC                                                23

(2) INFORMATION FOR SEQ ID NO:35:

(i) SEQUENCE CHARACTERISTICS:
        (A) LENGTH: 23 base pairs
        (B) TYPE: Nucleic acid
        (C) STRANDEDNESS: Not Relevant
        (D) TOPOLOGY: Linear (ii) MOLECULE TYPE: Synthetic DNA (xi) SEQUENCE DESCRIPTION: SEQ ID NO:35:

CGGCACGGAG GATTCTGGCC TGC                                                23

β-FRUCTOFURANOSIDASE AND ITS GENE, METHOD OF ISOLATING β-FRUCTOFURANOSIDASE GENE, SYSTEM FOR PRODUCING β-FRUCTOFURANOSIDASE, AND β-FRUCTOFURANOSIDASE VARIANT

This application is a 371 of PCT/JP97/00757, filed Mar. 11, 1997.

BACKGROUND OF THE INVENTION

1. Field of the Invention

The present invention relates to a β-fructofuranosidase gene, a process for isolating the gene, and a system for producing a β-fructofuranosidase. More particularly, the present invention relates to a novel β-fructofuranosidase, a DNA encoding it, and a process for isolating a DNA encoding β-fructofuranosidase; a novel mold fungus having no β-fructofuranosidase and a process for producing a recombinant β-fructofuranosidase using the mold fungus as a host; and a β-fructofuranosidase variant which selectively and efficiently produces a specific fructooligosaccharide such as 1-kestose from sucrose.

2. Description of the Related Art

The molecular structure of a fructooligosaccharide is the same as that of sucrose, except that the fructose half of a fructooligosaccharide is coupled with another one to three fructose molecules at positions C1 and C2 via a B bond. Fructooligosaccharides are indigestible sugars known for their physiological advantages, such as the facilitation of Bifidobacterial growth in the intestines, metabolic stimulation for cholesterols and other lipids, and little cariosity.

Fructooligosaccharides are found in plants, such as asparagus, onion, Jerusalem-artichoke and honey. They are also synthesized from sucrose by the newly industrialized mass production technique using fructosyltransfer reaction which is catalyzed by a β-fructofuranosidase derived from a microorganism. However, as β-fructofuranosidase preparations which are currently used for the industrial production of fructooligosaccharides is a cell-bound β-fructofuranosidase derived from *Aspergllus niger*. They contain a relatively large proportion of proteins as impurities. Therefore, a need still exists for a high-purity β-fructofuranosidase preparation with little unwanted proteins and a high titer. Further, an extracellular β-fructofuranosidase is desired in an attempt to improve efficiently by using it in a fixed form, as an extracellularly available enzyme is more suitable for fixation.

Genes encoding β-fructofuranosidase have been isolated from bacteria (Fouet, A., Gene, 45, 221–225 (1986), Martin, I. et al., Mol. Gen. Genet., 208, 177–184 (1987), Steininctz, M. et al., Mol. Gen. Genet., 191, 138–144 (1983), Scholle, R. et al., Gene, 80,49–56 (1989), Aslanidis, C. et al., J. Bacteriol., 171, 6753–6763 (1989), Sato, Y. and Kuramitsu, H. K., Infect. Immun., 56, 1956–1960 (1989), Gunasekaran, P. et al., J. Bacteriol., 172, 6727–6735 (1990)); yeast (Taussing, R, and M. Carlson, Nucleic Acids Res., 11, 1943–1954 (1983), Laloux, O. et al., FEBS Lett., 289, 64–68 (1991); mold (Boddy, L. M. et al., Curr, Genet., 24, 60–66 (1993); and plants (Arai, M. et al., Plant Cell Physiol., 33, 245–252 (1992), Unger, C. et al. Plant Physiol., 104, 1351–1357 (1994), Elliott, K. et al., Plant Mol. Biol., 21, 515–524 (1993), Sturm, A. and Chrispeels, M. J., Plant Cell, 2, 1107–1119 (1990)). However, to the best knowledge of the inventors, no gene has been found which encodes a β-fructofuranosidase having transferase activity and is usable for the industrial production of fructooligosaccharides.

If a β-fructofuranosidase gene usable for the industrial production of fructooligosaccharides is obtained, other functionally similar genes may be isolated, making use of their homology to the former. To the best knowledge of the inventors, no case has been reported on the screening of a new β-fructofuranosidase gene using this technique. A process for isolating a β-fructofuranosidase gene by this approach may also be applied to the screening of β-fructofuranosidase enzyme to achieve significantly less effort and time than in conventional processes: first, using a β-fructofuranosidase gene as a probe, a similar β-fructofuranosidase gene is isolated, making use of its homology to the former; then, the isolated gene is introduced and expressed in a host which does not metabolize sucrose, such as *Trichoderma viride*, or a mutant yeast which lacks sucrose metabolizing capability (Oda, Y. and Ouchi, K., Appl. Environ. Microbiol., 1989, 55, 1742–1747); a homogeneous preparation of β-fructofuranosidase is thus obtained as a genetic product with significantly less effort and time of screening. Furthermore, if the resultant β-fructofuranosidase exhibits desirable characteristics, its encoding gene may be introduced in a safe and highly productive strain to enable the production of the desired β-fructofuranosidase.

In addition, for producing such desirable β-fructofuranosidase, designing a system for production, particularly a host which does not metabolize sucrose, is an important consideration. Using a host which intrinsically has β-fructofuranosidase activity would result in a mixture of the endogenous β-fructofuranosidase of the host and the β-fructofuranosidase derived from the introduced gene. In this case, to take advantage of the β-fructofuranosidase derived from the introduced gene, it must be isolated from the endogenous β-fructofuranosidase of the host before application. On the contrary, using a host which lacks β-fructofuranosidase activity would eliminate the need for enzyme isolation. In other words, the resultant unpurified enzyme would show the desirable characteristics of the β-fructofuranosidase derived from the introduced gene. Known examples of microorganisms which do not have β-fructofuranosidase activity include the Trichoderma strains and yeast mutants lacking sucrose metabolizing capability (Oda, Y. Ibid.) as described above. However, considering that the resultant β-fructofuranosidase will be applied in food industry, a better candidate for a host would be a strain having no β-fructofuranosidase selected from Aspergillus mold fungi which have been time-tested for safety through application to foods and industrial production of enzymes.

Furthermore, if a β-fructofuranosidase gene usable for the industrial production of fructooligosaccharides is obtained, it may enable the development of a mutant with improved characteristics. For example, β-fructofuranosidase which produces 1-kestose selectively and efficiently would provide the following advantage:

The molecular structures of 1-kestose and nystose, which make up part industrially produced fructooligosaccharide mixtures of today, are the same as that of sucrose except that their fructose half is coupled with one and two molecules of fructose, respectively. It has been found recently that their high-purity crystals exhibit new desirable characteristics both in physical properties and food processing purpose while maintaining the general physiological advantages of fructooligosaccharides (Japanese Patent Application No. 222923/1995, Japanese Patent Laid-Open Publication No. 31160/1994). In this sense, they are fructooligosaccharide preparations having new features.

In consideration of the above, some of the inventors have proposed an industrial process for producing crystal 1-kestose from sucrose (Japanese Patent Application No. 64682/1996, Japanese Patent Application No.77534/ 1996, and Japanese Patent Application No. 77539/1996). According to this process, a β-fructofuranosidase harboring fructosyltransferase activity is first allowed to act on sucrose to produce 1-kestose; the resultant 1-kestose is fractionated to a purity of 80% or higher by chromatographic separation; then, using this fraction as a crystallizing sample, crystal 1-kestose is obtained at a purity of 95% or higher. The β-fructofuranosidase harboring fructosyltransferase activity used in this process should be able to produce 1-kestose from sucrose at a high yield while minimizing the byproduct nystose, which inhibits the reactions in the above steps of chromatographic separation and crystallization. In the enzyme derived from *Aspergillus niger*, which is currently used for the industrial production of fructooligosaccharide mixtures, the 1-kestose yield from sucrose is approximately 44%, while 7% is turned to nystose (Japanese Patent Application No. 64682/1996). These figures suggest that the enzyme has room for improvement in view of the industrial production of crystal 1-kestose. As a next step, new enzymes having more favorable characteristics were successfully screened from *Penicillium roqueforti* and *Scopulariopsis brevicaulis*. These enzymes were able to turn 47% and 55% of sucrose into 1-kestose, respectively, and 7% and 4% to nystose (Japanese Patent Application No. 77534/1996, and Japanese Patent Application No. 77539/1996). Although these figures show that the new enzymes were superior to the enzyme derived from *Aspergillus niger* for higher 1-kestose yields and less nystose production from sucrose, the productivity and stability of the enzymes were yet to be improved. Thus, it is awaited to see a new enzyme that maintains the productivity and stability of the enzyme derived from *Aspergillus niger*, which is currently used for the industrial production of fructooligosaccharide mixtures, while achieving a sucrose-to-1-kestose yield comparable or superior to that of the enzymes derived from *Penicillium roqueforti* and *Scopulariopsis brevicaulis*.

SUMMARY OF THE INVENTION

The inventors have now successfully isolated a novel β-fructofuranosidase gene, and developed a process for isolating other β-fructofuranosidase genes using the novel gene.

The inventors have also successfully produced a novel mold fungus having no β-fructofuranosidase activity, and developed a system for producing a recombinant β-fructofuranosidase using the mold fungus as a host.

Further, the inventors have found that the characteristics of β-fructofuranosidase with fructosyltransferase activity change with its amino acid sequence, and have successfully produced a β-fructofuranosidase variant which selectively and efficiently produces a specific fructooligosaccharide such as 1-kestose from sucrose.

The present invention is based on these findings.

Thus, the first aspect of the present invention provides a novel β-fructofuranosidase gene and a β-fructofuranosidase encoded by the gene.

The second aspect of the present invention provides a process for isolating a β-fructofuranosidase gene using the novel β-fructofuranosidase gene. The process according to the second aspect of the present invention also provides a novel β-fructofuranosidase.

In addition, the third aspect of the present invention provides a novel mold fungus having no β-fructofuranosidase activity and a system for producing a recombinant β-fructofuranosidase using the mold fungus as a host.

Further, the fourth aspect of the present invention provides a β-fructofuranosidase variant which selectively and efficiently produces a specific fructooligosaccharide such as 1-kestose from sucrose.

The β-fructofuranosidase according to the first aspect of the present invention has the amino acid sequence of SEQ ID No. 1 as shown in the sequence listing.

In addition, the β-fructofuranosidase gene according to the first aspect of the present invention encodes the amino acid sequence of SEQ ID No. 1 as shown in the sequence listing.

Further, the process for isolating a β-fructofuranosidase gene according to the second aspect of the present invention is a process for isolating a β-fructofuranosidase gene, making use of its homology to a nucleotide sequence comprising all or part of the nucleotide sequence of SEQ ID No. 2 as shown in the sequence listing.

In addition, a novel β-fructofuranosidase which has been isolated in the process according to the second aspect of the present invention is a polypeptide comprising the amino acid sequence of SEQ ID No. 11 or 13 as shown in the sequence listing or a homologue thereof.

Furthermore, the mold fungus according to the third aspect of the present invention is a mold fungus having no β-fructofuranosidase by deleting all or part of the β-fructofuranosidase gene on the chromosome DNA of the original Aspergillus mold fungus.

The β-fructofuranosidase variant according to the fourth aspect of the present invention is a mutant β-fructofuranosidase with fructosyltransferase activity obtained by a mutation in the original β-fructofuranosidase thereof, wherein the variant comprises an insertion, substitution or deletion of one or more amino acids in, or an addition to either or both of the terminals of, the amino acid sequence of the original β-fructofuranosidase, and the composition of the fructooligosaccharide mixture produced from sucrose as a result of fructosyltransfer reaction by the β-fructofuranosidase variant differs from the composition of the fructooligosaccharide mixture produced by the original β-fructofuranosidase.

DESCRIPTION OF THE PREFERRED EMBODIMENTS

Deposit of Microorganism

Figure 1:
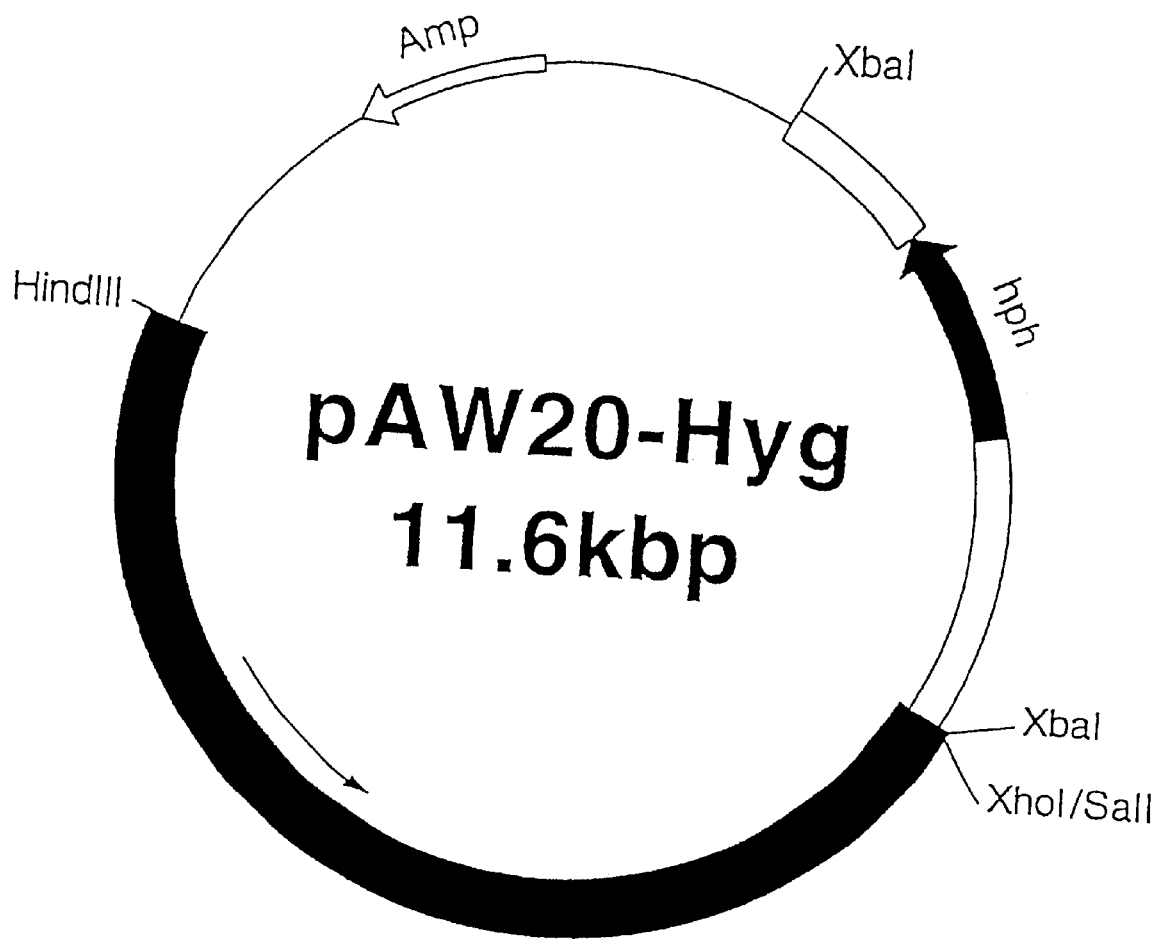
FIG. 1 shows expression vector pAW20-Hyg in which the β-fructofuranosidase gene according to the present invention has been introduced.

The novel mold fungus *Aspergillus niger* NIA1602 having no β-fructofuranosidase according to the present invention has been deposited in the National Institute of Bioscience and Human-Technology, Ministry of International Trade and Industry of Japan (Higashi 1-1-3, Tsukuba City, Ibaraki Pref., Japan) as of Mar. 6, 1997, under Accession No. FERM-BP5853.

β-Fructofuranosidase According to the First Aspect of the Present Invention

The polypeptide according to the first aspect of the present invention comprises the amino acid sequence of SEQ ID No. 1 as shown in the sequence listing. This polypeptide having the amino acid sequence of SEQ ID No. 1 has enzymatic activity as β-fructofuranosidase. The polypeptide according to the present invention involves a homologue of the amino acid sequence of SEQ ID No. 1 as shown in the sequence listing. The term "homologue" refers to an amino acid sequence in which one or more amino acids are inserted, substituted or deleted in, or added to either or both of the terminals of, the amino acid sequence of SEQ ID No. 1, while retaining β-fructofuranosidase activity. Such a homologue can be selected and produced by those skilled in the art without undue experiments by referring to the sequence of SEQ ID No. 1.

The β-fructofuranosidase having the amino acid sequence of SEQ ID No. 1 has a high fructosyltransferase activity and efficiently produces fructooligosaccharides. Specifically, when a sucrose solution at a concentration of 10 wt % or more is used as a substrate for reaction, the fructosyltransferase activity is at least 10 times higher than hydrolytic activity, with 50% or more changed to fructooligosaccharides.

Gene Encoding β-fructofuranosidase According to the First Aspect of the Present Invention The first aspect of the present invention provides, as a novel β-fructofuranosidase gene, a DNA fragment which comprises the nucleotide sequence encoding the amino acid sequence of SEQ ID No. 1.

A preferred embodiment of the present invention provides, as a preferred example of novel gene according to the present invention, a DNA fragment comprising the nucleotide sequence of SEQ ID No. 2 as shown in the sequence listing.

Generally, a nucleotide sequence which encodes the amino acid sequence of a given protein can be easily determined from the reference chart known as the "codon table." A variety of nucleotide sequences are available from those encoding the amino acid sequence of SEQ ID No. 1. Therefore, the term "a nucleotide sequence encoding the amino acid sequence of SEQ ID No. 1" refers to the meaning including the nucleotide sequence of SEQ ID No. 2, as well as nucleotide sequences which consist of the same codons as above allowing for degeneracy and encode the amino acid sequence of SEQ ID No. 1.

As described above, the present invention encompasses a homologue of the amino acid sequence of SEQ ID No. 1. Therefore, the DNA fragment according to the present invention involves a nucleotide sequence which encodes such a homologue.

As the nucleotide sequence of the DNA fragment according to the present invention is known, the DNA fragment may be obtained according to the procedure for the synthesis of a nucleic acid.

This sequence can be also obtained from *Aspergillus niger*, preferably *Aspergillus niger* ACE-2-1 (FERM-P5886 or ATCC20611), according to the procedure of genetic engineering. The specific process is described in more details later in Example A.

Expression of β-Fructofuranosidase Gene

The β-fructofuranosidase according to the first aspect of the present invention can be produced in a host cell which has been transformed by a DNA fragment encoding the enzyme. More specifically, a DNA fragment encoding the β-fructofuranosidase according to the first aspect of the present invention is introduced in a host cell in the form of a DNA molecule which is replicatable in the host cell and can express the above gene, particularly an expression vector, in order to transform the host cell. Then, the obtained transformant is cultivated.

Therefore, the present invention provides a DNA molecule which comprises a gene encoding the β-fructofuranosidase according to the present invention, particularly an expression vector. This DNA molecule is obtained by introducing a DNA fragment encoding the β-fructofuranosidase according to the present invention in a vector molecule. According to a preferred embodiment of the present invention, the vector is a plasmid.

The DNA molecule according to the present invention may be prepared by the standard technique of genetic engineering.

The vector applicable in the present invention can be selected as appropriate from viruses, plasmids, cosmid vectors, etc., considering the type of the host cell used. For example, a bacteriophage in the λ phage group or a plasmid in the pBR or pUC group may be used for *E. coli* host cells, a plasmid in the pUB group for *Bacillus subtilis*, and a vector in the YEp or YCp group for yeast.

It is preferable that the plasmid contain a selectable marker to ensure the selection of the obtained transformance, such as a drug-resistance marker or marker gene complementing an auxotrophic mutation. Preferred examples of marker genes include ampicillin-resistance gene, kanamycin-resistance gene, and tetracycline-resistance gene for bacterium host cells; N-(5'-phosphoribosyl)-anthranilate isomerase gene (TRP1), orotidine-5'-phosphate decarboxylase gene (URA3), and β-isopropylmalate dehydrogenase gene (LEU2) for yeast; and hygromycin-resistance gene (hph), bialophos-resistance gene (Bar), and nitrate reductase gene (niaD) for mold.

It is also preferable that the DNA molecule for use as an expression vector according to the present invention contain nucleotide sequences necessary for the expression of the β-fructofuranosidase gene, including transcription and translation control signals, such as a promoter, a transcription initiation signal, a ribosome binding site, a translation termination signal, and a transcription termination signal.

Examples of preferred promoters include, in addition to the promoter on the inserted fragment which is able to function in the host, promoters such as those of lactose operon (lac), and tryptophan operon (trp) for *E. coli*; promoters such as those of alcohol dehydrogenase gene (ADH), acid phosphatase gene (PHO), galactose regulated gene (GAL), and glyceraldehyde-3-phosphate dehydrogenase gene (GPD) for yeast; and promoters such as those of α-amylase gene (amy) and cellobiohydrolase I gene (CBHI) for mold.

When the host cell is *Bacillus subtilis*, yeast or mold, it is also advantageous to use a secretion vector to allow it to extracellularly secrete the produced recombinant β-fructofuranosidase. Any host cell with an established host-vector system may be used, preferably yeast, mold, etc. It is preferable also to use the mold fungus according to the third aspect of the present invention to be described later.

A novel recombinant enzyme produced by the transformant described above is obtained by the following procedure: first, the host cell described above is cultivated under suitable conditions to obtain the supernatant or cell bodies from the resultant culture, using a known technique such as centrifugation; cell bodies should be further suspended in a suitable buffer solution, then homogenized by freeze-and-thaw, ultrasonic treatment, or mortar, followed by centrifugation or filtration to separate a cell body extract containing the novel recombinant enzyme.

The enzyme can be purified by combining the standard techniques for separation and purification. Examples of such techniques include processes such as heat treatment, which rely on the difference in thermal resistance; processes such as salt sedimentation and solvent sedimentation, which rely on the difference in solubility; processes such as dialysis, ultrafiltration and gel filtration, and SDS-polyacrylamide gel electrophoresis, which rely on the difference in molecular weight; processes such as ion exchange chromatography, which rely on the difference in electric charge; processes such as affinity chromatography, which rely on specific affinity; processes such as hydrophobic chromatography and reversed-phase partition chromatography, which rely on the difference in hydrophobicity; and processes such as isoelectric focusing, which rely on the difference in isoelectric point.

Production of Fructooligosaccharides Using the β-fructofuranosidase According to the First Aspect of the Present Invention The present invention further provides a process for producing fructooligosaccharide using the recombinant host or recombinant β-fructofuranosidase described above.

In the process for producing fructooligosaccharides according to the present invention, the recombinant host or recombinant β-fructofuranosidase described above is brought into contact with sucrose.

The mode and conditions where the recombinant host or recombinant β-fructofuranosidase according to the present invention comes in contact with sucrose are not limited in any way provided that the novel recombinant enzyme is able to act on the sugar. A preferred embodiment for contact in solution is as follows: The sucrose concentration may be selected as appropriate in the range where the substrate sugar can be dissolved. However, considering the conditions such as the specific activity of the enzyme and reaction temperature, the concentration should generally fall in the range of 5 to 80%, preferably 30 to 70%. The temperature and pH for the reaction of the sugar by the enzyme should preferably be optimized for the characteristics of the novel recombinant enzyme. Therefore, the reasonable conditions are about 30 to 80° C., pH 4 to 10, preferably 40 to 70° C., pH 5 to 7.

The degree of purification of the novel recombinant enzyme may be selected as appropriate. The enzyme may be used either as unpurified in the form of supernatant from a transformant culture or cell body homogenate, as purified after processed in various purification steps, or as isolated after processed by various purification means.

Furthermore, the enzyme may be brought into contact with sucrose as fixed on a carrier using the standard technique.

The fructooligosaccharides thus produced is purified from the resulting solution according to a known procedure. For example, the solution may be heated to deactivate the enzyme, decolorized using activated carbon, then desalted using ion exchange resin.

Process for Isolating a β-fructofuranosidase Gene According to the Second Aspect of the Present Invention In the process for isolating a gene according to the second aspect of the present invention, the nucleotide sequence of SEQ ID No. 2 is used.

The process for isolating a gene according to the second aspect of the present invention makes use of its homology to a nucleotide sequence comprising all or part of the nucleotide sequence of SEQ ID No. 2 as shown in the sequence listing. Examples of such processes include:

a) screening a gene library which presumably contains a β-fructofuranosidase gene using the nucleotide sequence as a probe.

b) preparing a primer based on the nucleotide sequence information, then performing PCR using a sample which presumably contains a β-fructofuranosidase gene as a template.

More specifically, process a) above comprises:

preparing a gene library which presumably contains a β-fructofuranosidase gene, screening the gene library using a nucleotide sequence comprising all or part of the nucleotide sequence of SEQ ID No. 2 as shown in the sequence listing to select sequences which hybridize with the nucleotide sequence comprising all or part of the nucleotide sequence of SEQ ID No. 2 as shown in the sequence listing from the gene library, then isolating the selected sequences, and isolating a β-fructofuranosidase gene from the sequences which have been selected and isolated from the gene library.

The gene library may be a genomic DNA library or a cDNA library, and may be prepared according to a known procedure.

It is preferable that the nucleotide sequence comprising all or part of the nucleotide sequence of SEQ ID No. 2 for use in screening the gene library be a nucleotide sequence comprising part of the nucleotide sequence of SEQ ID No. 2, or a probe. Preferably, the probe should be marked.

The procedures for screening the gene library, marking the probe, isolating the marked and selected sequences, and further isolating a β-fructofuranosidase gene from the isolated sequences may be performed according to the standard techniques of genetic engineering under suitably selected conditions. Those skilled in the art would be able to select these procedures and conditions easily by referring to the sequence of SEQ ID No. 2.

On the other hand, process b) above comprises:

preparing a primer consisting of a nucleotide sequence which comprises all or part of the nucleotide sequence of SEQ ID No. 2 as shown in the sequence listing, carrying out PCR process on the primer using a sample which presumably contains a β-fructofuranosidase gene as a template, and isolating a β-fructofuranosidase gene from the amplified PCR product.

The procedures for preparing the primer to be used, for preparing a sample which presumably contains a β-fructofuranosidase gene, and for PCR may be performed according to the standard techniques of genetic engineering under suitably selected conditions. Those skilled in the art would be able to select these procedures and conditions easily by referring to the sequence of SEQ ID No. 2.

The scope of application of the process for isolating a β-fructofuranosidase gene according to the present invention is not limited in any way provided that β-fructofuranosidase is presumably contained, such as Eumycetes, specifically Aspergillus, Penicillium or Scopulariopsis microorganisms.

Novel β-fructofuranosidase and Gene Encoding Same Obtained by the Second Aspect of the Present Invention The process for isolating a gene according to the second aspect of the present invention provides a novel β-fructofuranosidase enzyme having the amino acid sequence of SEQ ID No. 11 or 13 as shown in the sequence listing.

The β-fructofuranosidase enzyme according to the present invention may be a homologue of the amino acid sequence of SEQ ID No. 11 or 13 as shown in the sequence listing. The term "homologue" refers to an amino acid sequence in which one or more amino acids are inserted, substituted or deleted in, or added to either or both of the terminals of, the amino acid sequence of SEQ ID No. 11 or 13, while retaining β-fructofuranosidase activity. Such a homologue can be selected and produced by those skilled in the art without undue experiments by referring to the sequence of SEQ ID No. 11 or 13.

The β-fructofuranosidase having the amino acid sequence of SEQ ID No. 11 or 13 has a high fructosyltransferase activity and efficiently produces fructooligosaccharides. Specifically, when a sucrose solution at a concentration of 30% or more is used as a substrate for reaction, the fructosyltransferase activity is at least 4 times and 7 times higher, respectively, than hydrolytic activity, with 50% or more changed to fructooligosaccharides.

The novel β-fructofuranosidase gene provided by the process for isolating a gene according to the second aspect of the present invention comprises a nucleotide sequence encoding the amino acid sequence of SEQ ID No. 11 or 13 as shown in the sequence listing or a homologue thereof.

Generally, a nucleotide sequence which encodes the amino acid sequence of a given protein can be easily determined from the reference chart known as the "codon table." Then, a variety of nucleotide sequences are available from those encoding the amino acid sequence of SEQ ID No. 11 or 13. Therefore, the term "a nucleotide sequence encoding the amino acid sequence of SEQ ID No. 11 or 13" refers to the meaning including the nucleotide sequence of SEQ ID No. 12 or 14, as well as nucleotide sequences which consist of the same codons as above allowing for degeneracy and encode the amino acid sequence of SEQ ID No. 11 or 13.

A preferred embodiment of the present invention provides a DNA fragment comprising the nucleotide sequence of SEQ ID No. 12 or 14 as shown in the sequence listing as preferred examples of the novel gene according to the present invention.

As described above, the enzyme encoded by the novel gene according to the present invention involves a homologue of the amino acid sequence of SEQ ID No. 11 or 13. Therefore, the DNA fragment according to the present invention may be a nucleotide sequence which encodes such a homologue.

As the nucleotide sequence is known for the DNA fragment according to the present invention, the DNA fragment may be obtained according to procedure for the synthesis of a nucleic acid.

The sequence can be obtained from *Penicillium roqueforti* or *Scopulariopsis brevicaulis*, preferably *Penicillium roqueforti* IAM7254 or *Scopulariopsis brevicaulis* IFO4843, using the procedures of genetic engineering. The specific process is described in more details later in Example B.

Aspergillus Mold Fungus Having no β-fructofuranosidase According to the Third Aspect of the Present Invention and Preparation Thereof An Aspergillus mold fungus having no β-fructofuranosidase according to the third aspect of the present invention refers to an Aspergillus mold fungus whose culture's supernatant and/or cell body homogenate provides unpurified enzyme which, when allowed to react with sucrose, does not change the substrate sucrose.

Such a mold fungus is obtained by deactivating a β-fructofuranosidase gene, deactivating the mechanism involved in the expression of a β-fructofuranosidase gene, or deactivating the mechanism involved in the synthesis and secretion of the β-fructofuranosidase protein.

However, it is preferable that the β-fructofuranosidase gene itself be deactivated, in view of the stability of mutation and the productivity of enzyme. It is especially preferable that all or part of the region encoding β-fructofuranosidase be deleted.

Available procedures for preparing such a mold fungus include the use of a mutagen such as NTG (1-methyl-3-nitro-1-nitrosoguanidine) or ultraviolet rays to induce mutation in the original Aspergillus mold fungus. However, a process using the DNA recombination technology is preferred.

Examples of procedures for deactivating a β-fructofuranosidase gene using DNA recombination technology include methods using homologous recombination, which are subdivided into two types of methods: one-step gene targeting and two-step gene targeting.

In one-step gene targeting, an insertion vector or substitution vector is used.

As an insertion vector, a vector bearing a deactivated β-fructofuranosidase gene and a selectable marker gene for selecting the transformants is prepared. The deactivated β-fructofuranosidase gene is the same as the original β-fructofuranosidase gene except that it contains two discrete mutations (preferably deletions) which can independently deactivate the target β-fructofuranosidase gene.

This insertion vector is introduced in the cell to induce homologous recombination with the target β-fructofuranosidase gene on the chromosome between the two mutations. As a result, the chromosome now has two copies of the target β-fructofuranosidase gene, each having one mutation. The target β-fructofuranosidase gene is thus deactivated.

When using a substitution vector, a vector bearing the target β-fructofuranosidase gene which has been split by introducing a selectable marker gene is prepared.

The substitution vector is introduced in the cell to induce homologous recombination at two locations, with the selection marker in-between, in the region derived from the β-fructofuranosidase gene. As a result, the target β-fructofuranosidase gene on the chromosome is replaced with the gene containing the selectable marker gene and, thus, deactivated.

The two-step gene targeting is achieved either by direct substitution or hit-and-run substitution.

The first step of direct substitution is the same as the procedure using a substitution vector in one-step gene targeting. In the second step, a vector which bears a deactivated β-fructofuranosidase gene containing at least one mutation (preferably a deletion) which can independently deactivate the target β-fructofuranosidase gene is prepared. This vector is then introduced in the cell to induce homologous recombination at two locations, with the mutation in-between, in the target β-fructofuranosidase gene on the chromosome, which has been split by the selectable marker gene. As a result, the target β-fructofuranosidase gene on the chromosome is replaced with the deactivate target β-fructofuranosidase gene. These recombinant strains can be selected with the absence of the marker gene as an index.

In the first step of hit-and-run substitution, a vector which bears a deactivated β-fructofuranosidase gene containing at least one mutation (preferably a deletion) which can independently deactivate the target β-fructofuranosidase gene and a selectable marker gene is prepared. This vector is then introduced in the cell to induce homologous recombination with the β-fructofuranosidase gene on the chromosome in the target β-fructofuranosidase gene on the upstream of the mutation. As a result, the vector bearing the selectable marker gene is now positioned between two copies of target β-fructofuranosidase gene on the chromosome—one with a mutation and one without. Next, the vector between the two copies of target β-fructofuranosidase gene is looped out, and allowed to homologously recombine again on the downstream of the mutation. As a result, the vector bearing the selectable marker gene and one copy of target β-fructofuranosidase gene is removed, leaving the target β-fructofuranosidase gene on the chromosome with a mutation. These recombinant strains can be selected with the absence of the marker gene as in index. It should be noted that the same effect is obviously achievable by inducing homologous recombination first on the downstream of the mutation, then on its upstream.

In the above procedures, any selectable marker gene may be used provided that a transformant is selectable. However, strains missing the selectable marker should be selected in the course of two-step gene targeting, it is preferable to use a selectable marker gene which allows these strains to be positively selected, such as nitrate reductase gene (niaD), orotidine-5'-phosphate decarboxylase gene (pyrG), or ATP sulfurylase gene (sC).

Examples of mold fungus according to the third aspect of the present invention include *Aspergillus niger* NIA1602 (FERM BP-5853).

Process for Producing a Recombinant β-fructofuranosidase Using the Mold Fungus Having no β-fructofuranosidase According to the Third Aspect of the Present Invention as a Host The mold fungus according to the present invention may preferably be used for producing recombinant β-fructofuranosidase. More specifically, a DNA fragment encoding β-fructofuranosidase is introduced into the mold fungus according to the present invention in the form of a DNA molecule which is replicable in the host cell according to the present invention and can express the gene, particularly an expression vector, in order to transform the mold fungus. The transformant has then the ability to produce the recombinant β-fructofuranosidase and no other β-fructofuranosidase enzymes.

This procedure, where a preferred from of the DNA molecule is a plasmid, may be carried out according to the standard techniques of genetic engineering.

According to a preferred embodiment of the present invention, examples of DNA fragments encoding β-fructofuranosidase include the DNA encoding β-fructofuranosidase according to the first aspect of the present invention as described earlier, the DNA encoding a novel β-fructofuranosidase which has been isolated in the process according to the second aspect of the present invention, and the DNA encoding a β-fructofuranosidase variant according to the fourth aspect of the present invention as described later.

Examples of systems for expressing β-fructofuranosidase using the mold fungus according to the third aspect as a host include the expressing system which has been described in the first aspect of the present invention.

More specifically, it is preferable that the plasmid to be used bear a selectable marker gene for the transformant, such as a drug-resistance marker gene or marker gene complementing an auxotrophic mutation. Examples of preferred marker genes include hygromycin-resistance gene (hph), bialophos-resistance gene (Bar), nitrate reductase gene (niaD), orotidine-5'-phosphate decarboxylase gene (pyrG), and ATP-sulfurylase gene (sC).

It is also preferable that the DNA molecule for use as an expression vector contain nucleotide sequences necessary for the expression of the β-fructofuranosidase gene, including transcription and translation control signals, such as a promoter, a transcription initiation signal, a translation termination signal, and a transcription termination signal. Examples of preferred promoters include, in addition to the promoter on the inserted fragment which is able to function in the host according to the present invention, promoters such as those of α-amylase gene (amy), glucoamylase gene (gla), β-fructofuranosidase gene, glyceraldehyde-3-phosphatase dehydrogenase gene (gpd), and phosphoglycerate kinase gene (pgk).

It is also advantageous to use a secretion vector as the expression vector to allow it to extracellularly secrete the produced recombinant β-fructofuranosidase.

In the system for producing β-fructofuranosidase using a mold fungus according to the third aspect of the present invention, the transformed mold fungus according to the present invention is first cultivated under suitable conditions. The culture is treated by a known procedure such as centrifugation to obtain the supernatant or cell bodies. Cell bodies should be further suspended in a suitable buffer solution, then homogenized by freeze-and-thaw, ultrasonic treatment, or mortar, followed by centrifugation or filtration to separate a cell body extract containing the novel recombinant β-fructofuranosidase.

β-Fructofuranosidase Variant According to the Fourth Aspect of the Present Invention The β-fructofuranosidase variant according to the fourth aspect of the present invention is obtained by the mutation of the original β-fructofuranosidase. In the present invention, the mutation comprises an insertion, substitution or deletion of one or more amino acids in, or an addition to either or both of the terminals of, the amino acid sequence of the original β-fructofuranosidase, while the composition of the fructooligosaccharide mixture produced from sucrose as a result of fructosyltransfer reaction by the β-fructofuranosidase variant differs from the composition of the fructooligosaccharide mixture produced by the original β-fructofuranosidase.

Although the source of the original β-fructofuranosidase is not limited in any way in the present invention provided that the β-fructofuranosidase has fructosyltransferase activity, it is preferable to use β-fructofuranosidase derived from Eumycetes, particularly Aspergillus, Penicillium, Scopulariopsis, Fusarium or Aureobasidium. The most preferable β-fructofuranosidase is one derived from Aspergillus, particularly the β-fructofuranosidase consisting of the amino acid sequence of SEQ ID No. 1 as shown in the sequence listing according to the first aspect of the present invention or a homologue thereof. The original β-fructofuranosidase may also be the β-fructofuranosidase which is obtained by the aforementioned isolating process according to the second aspect of the present invention or a homologue thereof.

According to a preferred embodiment of the present invention, if the original β-fructofuranosidase consists of the amino acid sequence of SEQ ID No. 1, one such example is a variant in which one or more amino acids selected from the group consisting of amino acid residues at positions 170, 300, 313 and 386 in the amino acid sequence are substituted by other amino acid residues.

According to a preferred embodiment of the present invention, preferred examples include variants in which:

the amino acid residue at position 170 is substituted by an aromatic amino acid selected from the group consisting of tryptophan, phenylalanine and tyrosine, most preferably tryptophan;

the amino acid residue at position 300 is substituted by an amino acid selected from the group consisting of tryptophan, valine, glutamic acid and aspartic acid;

the amino acid residue at position 313 is substituted by a basic amino acid selected from the group consisting of lysine, arginine and histidine, most preferably lysine or arginine; and the amino acid residue at position 386 is substituted by a basic amino acid selected from the group consisting of lysine, arginine and histidine, most preferably lysine. These variants are advantageous in that they can produce 1-kestose selectively and efficiently from sucrose.

The variants according to a more preferred embodiment of the present invention are those in which amino acid residues at positions 170, 300 and 313 are substituted by tryptophan, tryptophan and lysine, respectively, or by tryptophan, valine and lysine, respectively. These variants are advantageous in that they can produce 1-kestose more selectively, and efficiently from sucrose.

If the original β-fructofuranosidase is a homologue of the amino acid sequence of SEQ ID No. 1, one such example is a variant in which one or more amino acid residues equivalent to the amino acid residues at positions 170, 300, 313 and 386 in the amino acid sequence of SEQ ID No. 1 are substituted by other amino acids. The amino acids to be substituted in a homologue of the original β-fructofuranosidase consisting of the amino acid sequence of SEQ ID No. 1 are easily selected by comparing amino acid sequences by a known algorithm. If, however, comparison of amino acid sequences by a known algorithm is difficult, the amino acids to be substituted can be easily determined by comparing the stereochemical structures of the enzymes.

Preparation of a Variant β-fructofuranosidase According to the Fourth Aspect of the Present Invention The variant β-fructofuranosidase according to the fourth aspect of the present invention may be prepared by procedures such as genetic engineering or polypeptide synthesis.

When employing genetic engineering, the DNA encoding the original β-fructofuranosidase is first obtained. Next, mutation is induced at specific sites on the DNA to substitute their encoded amino acids. Then, an expression vector containing the mutant DNA is introduced in a host cell to transform it. The transformant cell is cultivated to prepare the desired β-fructofuranosidase variant.

Several methods are known to those skilled in the art for inducing mutation at specific sites on a gene, such as the gapped duplex method (Methods in Enzymology, 154, 350 (1987)) and the Kunkel method (Methods in Enzymology, 154, 367 (1987)). These methods are applicable for the purpose of inducing mutation at specific sites on a DNA encoding β-fructofuranosidase. The nucleotide sequence of the mutant DNA may be identified by procedures such as the chemical degradation method devised by Maxam and Gilbert (Methods in Enzymology, 65, 499 (1980)) or the dideoxynucleotide chain termination method (Gene, 19, 269 (1982)). The amino acid sequence of the β-fructofuranosidase variant can be decoded from the identified nucleotide sequence.

Production of a β-fructofuranosidase Variant According to the Fourth Aspect of the Present Invention The β-fructofuranosidase variant according to the fourth aspect of the present invention may be produced in a host cell by introducing a DNA fragment encoding β-fructofuranosidase in the host cell in the form of a DNA molecule which is replicable in the host cell and can express the gene, particularly an expression vector, in order to transform the host cell.

Therefore, the present invention provides a DNA molecule, particularly an expression vector, which comprises a gene encoding the β-fructofuranosidase variant according to the present invention.

The DNA molecule is obtained by introducing a DNA fragment encoding the β-fructofuranosidase variant according to the present invention in a vector molecule. According to a preferred embodiment of the present invention, the vector is a plasmid.

The DNA molecule according to the present invention may be prepared by the standard technique of genetic engineering.

The vector applicable in the present invention may be selected as appropriate, considering the type of the host cell used, from viruses, plasmids, cosmid vectors, etc. For example, a bacteriophage in the λ phage group or a plasmid in the pBR or pUC group may be used for *E. coli* host cells, a plasmid in the pUB group for *Bacillus subtilis*, and a vector in the YEp, YRp or YCp group for yeast.

It is preferable that the plasmid contain a selectable marker to ease the selection of the transformant, such as a drug-resistance marker or marker gene complementing an auxotrophic mutation.

Preferred examples of marker genes include ampicillin-resistance gene, kanamycin-resistance gene, and tetracycline-resistance gene for bacterium host cells; N-(5'-phosphoribosyl)-anthranilate isomerase gene (TRP1), orotidine-5'-phosphate decarboxylase (URA3), and β-isopropylmalate dehydrogenase gene (LEU2) for yeast; and hygromycin-resistance gene (hph), bialophos-resistance gene (Bar), and nitrate reductase gene (niaD) for mold.

It is also preferable that the DNA molecule for use as an expression vector according to the present invention contain nucleotide sequences necessary for the expression of the β-fructofuranosidase gene, including transcription and translation control signals, such as a promoter, a transcription initiation signal, a ribosome binding site, a translation termination signal, and a transcription termination signal.

Examples of preferred promoters include, in addition to the promoter on the inserted fragment which is able to function in the host, promoters such as those of lactose operon (lac), and tryptophan operon (trp) for *E. coli*; promoters such as those of alcohol dehydrogenase gene (ADH), acid phosphatase gene (PHO), galactose regulated gene (GAL), and glyceraldehyde-3-phosphate dehydrogenase gene (GPD) for yeast; and promoters such as those of α-amylase gene (amy), glucoamylase gene (gla), cellobiohydrolase gene (CBHI), and β-fructofuranosidase gene for mold.

If the host cell is *Bacillus subtilis*, yeast or mold, it is also advantageous to use a secretion vector to allow it to extracellularly secrete recombinant β-fructofuranosidase. Any host cell with an established host-vector system may be used, preferably yeast, mold, etc. The use of a host cell without sucrose metabolizing capability would be particularly preferred, as it does not have an enzyme which acts on sucrose except the expressed β-fructofuranosidase variant and, therefore, allows the resultant β-fructofuranosidase variant to be used for the production of fructooligosaccharides without purification. Thus, according to a preferred embodiment of the present invention, the mold fungus according to the third aspect of the present invention may be used as the host cell. A few Trichoderma strains and a type of yeast may be used as the host without sucrose metabolizing capability (Oda, Y. and Ouchi, K., Appl. Environ. Microbiol., 55, 1742–1747, 1989).

Production of Fructooligosaccharides Using the β-fructofuranosidase Variant According to the Fourth Aspect of the Present Invention The present invention further provides a process for producing fructooligosaccharides using the β-fructofuranosidase variant. The process for producing fructooligosaccharides is practiced by bringing the host cell which synthesizes the β-fructofuranosidase variant, or the β-fructofuranosidase variant itself into contact with sucrose.

In the process using the β-fructofuranosidase variant, fructooligosaccharides may be produced and purified under substantially the same conditions as in the process for producing fructooligosaccharides using the β-fructofuranosidase according to the first aspect of the present invention.

EXAMPLES

The present invention will now be described in more detail using the following Examples. However, the Examples are merely illustrative in nature and should not be construed to limit the spirit and scope of the claims.

Example A

Example A1
Purification and Partial Sequencing of β-fructofuranosidase

An electrophoretically homogeneous sample of β-fructofuranosidase was obtained from the cell bodies of *Aspergillus niger* ACE-2-1 (ATCC20611) by purifying it according to the process described in Agric. Biol. Chem., 53, 667–673 (1989).

The purified enzyme was digested with lysyl endopeptidase (SKK Biochemicals Corp.). The resultant peptides were collected by HPLC (Waters) using a TSK gel ODS120T column (Tosoh Corp.), and sequenced using a protein sequencer (Shirnmadzu Corp.). As a result, four partial amino acid sequences were determined as shown in the sequence listing (SEQ ID Nos. 3 to 6).

The N-terminal of the enzyme protein before digested with lysyl endopeptidase was determined by using the protein sequencer as shown in the sequence listing (SEQ ID No.17).

Example 2A
Purification of Partial DNA Fragment of β-fructofuranosidase Gene by PCR

*Aspergillus niger* ACE-2-1 (ATCC20611) was cultivated in a YPD medium (1% yeast extract, 2% polypepton and 2% glucose), then collected and freeze-dried. The homogenate was mixed with 8 ml of TE buffer solution (10 mM Tris-HCl (pH 8.0) and 1 mM EDTA), then with 4 ml of TE buffer solution containing 10% SDS, and maintained at 60° C. for 30 minutes. Next, the solution was intensely shaken with a 12 ml mixture of phenol, chloroform and isoamyl alcohol (25:24:1), followed by centrifugation. The aqueous layer was transferred to another container, and mixed with 1 ml of 5M potassium acetate solution. After stored in an iced water bath for at least 1 hour, the solution was centrifuged. The aqueous layer was transferred to another container, and mixed with 2.5-fold volume of ethanol to sediment. The precipitate was dried and dissolved in 5 ml of TE buffer solution. After 5 µl of 10 mg/ml RNase A (Sigma Chemical Co.) solution was added, the mixture was maintained at 37° C. for 1 hour. Then, 50 µl of 20 mg/ml proteinase K (Wako Pure Chemical Industries, Ltd.). solution was added, and the mixture was maintained at 37° C. for 1 hour. Next, 3 ml of PEG solution (20% polyethylene glycol 6000 and 2.5 M sodium chloride) was added to sediment the DNA. The precipitate was dissolved in 500 µl of TE buffer solution, and extracted twice with a mixture of phenol, chloroform and isoamyl alcohol, then allowed to sediment in ethanol. This precipitate was washed in 70% ethanol, dried, then dissolved in an adequate amount of TE buffer solution (chromosomal DNA sample).

PCR was performed using Perkin Elmer Cetus DNA Thermal Cycler as follows: The chromosomal DNA, 0.5 µl (equivalent to 1 µg), which had been prepared above, was mixed with 10 µl of buffer solution [500 mM KCl, 100 mM Tris-HCl (pH 8.3), 15 mM MgCl$_2$ and 1% Triton X-100], 8 µl of 2.5 mM dNTP solution, 1 µl each of 1 mM positive-chain DNA primer of SEQ ID No. 8 as shown in the sequence listing (primer #1) and negative-chain DNA primer of SEQ ID No. 9 as shown in the sequence listing (primer #2), 0.5 µl Taq DNA polymerase (Wako Pure Chemical Industries, Ltd.), and 79 µl of sterilized water, to a total volume of 100 µl. After pretreatment at 94° C. for 5 minutes, the sample was incubated at 94° C. for 1 minute (degeneration step), at 54° C. for 2 minutes (annealing step), and at 72° C. for 3 minutes (extending step), for a total of 25 reaction cycles. The last cycle was followed by incubation at 72° C. for 7 minutes. The sample was then extracted with a mixture of phenol, chloroform and isoamyl alcohol, and allowed to sediment in ethanol. The precipitate was dissolved in 20 µl of TE buffer solution and electrophoresed through agarose gel. The specifically amplified band at about 800 bp was cut out using the standard technique. The recovered DNA fragment was allowed to sediment in ethanol.

After the DNA precipitate was dissolved in 8 µl of sterilized water, its terminals were blunted by using DNA Blunting Kit (Takara Shuzo Co., Ltd.). Then, after the 5' terminal was phosphorylated using T4 DNA kinase (Nippon Gene), the sequence was cloned to the SmaI site of pUC119. The fragment inserted in the plasmid was sequenced using a fluorescence sequencer, ALFred DNA Sequencer (Pharmacia), as shown in the sequence listing (SEQ ID No. 10). The total length of the PCR fragment was 788 bp. The first 14 amino acids on the N terminal of the amino acid sequence encoded by this DNA fragment corresponded to amino acids No. 7 to 20 of SEQ ID No. 3 as shown in the sequence listing, while amino acids No. 176 to 195 on the N terminal corresponded to amino acids No. 1 to 20 of SEQ ID No. 4 as shown in the sequence listing. Further, the first 10 amino acids on the C terminal of the same sequence corresponded to amino acids No. 1 to 10 of SEQ ID No. 5 as shown in the sequence listing. Thus, the amino acid sequence was identical to that determined from the purified β-fructofuranosidase.

Example A3
Screening of Clone Containing Complete DNA Fragment Encoding β-fructofuranosidase About 10 µg of chromosome DNA sample which had been prepared in Example A2 above was digested with EcoRI, followed by agarose gel electrophoresis, then blotted on a Hybond-N+ membrane (Amersham International)

according to the procedure described in Molecular Cloning (Cold Spring Harbour, 1982)

This membrane was subjected to Southern analysis using ECL Direct DNA/RNA Labelling & Detection System (Amersham International), with the 788 bp PCR fragment prepared in Example A2 above used as a probe. As a result, a DNA fragment of about 15 kbp hybridized with the probe.

In the next step, about 20 µg of chromosomal DNA sample above was digested with EcoRI, followed by agarose gel electrophoresis. DNA fragments at about 15 kbp were separated and recovered according to the procedure described in Molecular Cloning (Ibid.).

The recovered DNA fragments of about 15 kbp (about 0.5 µg) were ligated with 1 µg of λDASH II, which had been digested with both of HindIII and EcoRI, and packaged using an in vitro packaging kit, GIGAPACK II Gold (Stratagene L.L.C.), then introduced in *E. coli* XLI-Blue MRA (P2), to prepare a library.

As a result of plaque hybridization using ECL Direct DNA/RNA Labelling & Detection System (Amersham International) with the 788 bp PCR fragment above used as a probe, 25 clones turned out positive in 15,000 plaques. Three of the positive clones were purified by a second screening to prepare phage DNA, which was then analyzed using restriction enzymes. The result showed that all the clones had an identical EcoRI fragment of about 15 kbp.

This EcoRI fragment of about 15 kbp was subdivided into a smaller fragment to select the desired DNA region using restriction enzymes, then subcloned to plasmid vector pUC118 or pUC119. The plasmid DNA was obtained from the subclone according to the standard procedure and sequenced as in Example A2 using a fluorescence sequencer, ALFred DNA Sequencer (Pharmacia), as shown in the sequence listing (SEQ ID No. 2).

Example A4

Expression of β-fructofuranosidase Gene by *Trichoderma viride*

An about 5.5 kbp HindIII-XhoI fragment containing a gene encoding β-fructofuranosidase was prepared from the phage DNA obtained in Example A3. The fragment was ligated with the HindIII-SalI site of plasmid vector pUC119 (plasmid pAW20).

Further, plasmid pDH25 (D. Cullen et al., (1987) Gene, 57, 21–26) was partially digested with EcoRI and ligated with XbaI linker, and digested again with XbaI. Then, a 3 kbp XbaI fragment which consisted of the promoter and terminator of the trpC gene derived from *Aspergillus nidulans* and hygromycin B phosphotransferase gene derived from *E. coli* was prepared as a hygromycin-resistance gene cassette. The fragment was inserted into the XbaI site of plasmid pAW20 (plasmid pAW20-Hyg in FIG. 1).

*Trichoderma viride* was cultivated in a seed medium (3% glucose, 0.1% polypepton, 1% yeast extract, 0.14% ammonium sulfate, 0.2% potassium dihydrogenphosphate and 0.03% magnesium sulfate) at 28° C. for 20 hours. The resultant mycelium was collected by centrifugation at 3000 rpm for 10 minutes and washed twice in 0.5 M sucrose solution.

The mycelium was suspended in 0.5 M sucrose solution containing 5 mg/ml Cellularse-Onozuka R-10 (SKK Biochemicals Corp.) and 5 mg/ml of Novozym 234 (Novo Nordisk), and gently shaken at 30° C. for 1 hour to form protoplasts. After the cell body residue was filtered out, the suspension was centrifuged at 2500 rpm for 10 minutes. The collected protoplasts were washed twice in SUTC buffer solution (0.5 M sucrose, 10 mM Tris-HCl (pH 7.5) and 10 mM calcium chloride) and suspended in the buffer solution to a final concentration of $10^7$/ml.

The protoplast suspension, 100 µl, was mixed with 10 µl of DNA solution, which had been dissolved in TE buffer solution so that the concentration of plasmid pAW20-Hyg would be 1 mg/ml, and iced for 5 minutes. Then, it was mixed with 400 µl of PEG solution (60% polyethylene glycol 4000, 10 mM Tris-HCl (pH 7.5) and 10 mM calcium chloride), and iced for an additional 20 minutes. Next, the protoplasts were washed in SUTC buffer solution, and laid on a potato dextrose agar medium (Difco) containing 100 µg/ml hygromycin B and 0.5 M sucrose, together with a potato dextrose soft agar medium containing 0.5 M sucrose, and incubated at 28° C. for 5 days. The appeared colonies were selected as transformants.

After the transformant and the original strain were cultivated in the seed medium at 28° C. for 4 days, the β-fructofuranosidase activity of the culture supernatant was measured according to the method described in Agric. Biol. Chem., 53, 667–673 (1989). As a result, the original strain turned out negative for the activity, while the transformant exhibited $1\times10^2$ units/ml of activity.

Example B

Example B1

Southern Analysis of Chromosomal DNA from β-fructofuranosidase-producing Fungi (1) Preparation of DNA fragment for use as probe A DNA fragment for use as a probe was prepared by PCR, with plasmid pAW20-Hyg containing the nucleotide sequence of SEQ ID No. 2 as shown in the sequence listing as template DNA. PCR was performed with Perkin Elmer Cetus DNA Thermal Cycler as follows: The plasmid DNA pAW20-Hyg), 0.5 µl (equivalent to 0.1 µg), which had been prepared above, was mixed with 10 µl of reaction buffer solution [500 mM KCl, 100 mM Tris-HCl (H 8.3), 15 mM MgCl$_2$ and 1% Triton X-100], 8 µl of 2.5 mM dNTP solution, 2 µl each of 0.01 mM positive-chain DNA primer of SEQ ID No. 15 as shown in the sequence listing (primer #1) and negative-chain DNA primer of SEQ ID No. 16 as shown in the sequence listing (primer #2), 0.5 µl Taq DNA polymerase (Wako Pure Chemical Industries, Ltd.), and 77 µl of sterilized water, to a total volume of 100 µl. After pretreatment at 94° C. for 5 minutes, the sample was incubated at 94° C. for 1 minute (degeneration step), at 54 C for 2 minutes (annealing step), and at 72°°C. for 3 minutes (extending step), for a total of 25 reaction cycles. The last cycle was followed by incubation at 72° C. for 7 minutes. The sample was then extracted with a mixture of phenol, chloroform and isoamyl alcohol, and allowed to sediment in ethanol. The precipitate was dissolved in 20 µl of TE buffer solution and electrophoresed through agarose gel. The specifically amplified band at about 2 kbp was cut out using the standard technique. The recovered DNA fragment was allowed to sediment in ethanol. The DNA precipitate was dissolved in sterilized water to a concentration of 0.1 µg/µl to obtain a sample solution.

(2) Preparation and Southern Analysis of chromosomal DNA from β-fructofuranosidase-producing fungi Mold fungus strains having the capability to produce β-fructofuranosidase: *Aspergillus japonicus* IFO4408, *Aspergillus aculeatus* IFO31348, *Penicillium roqueforti* IAM7254, *Scopulariopsis brevicaulis* IFO4843, IFO5828, IFO5841, IFO6588, IFO31688 and IFO31915, *Scopulariopsis brevicaulis* var. *glabra* IFO7239, and *Scopulariopsis roseola* IFO7564, were cultivated in a YPD liquid medium (1% yeast extract, 2% polypepton and 2% glucose) at 28° C. for 2 days. From the resultant cell bodies, the chromosomal DNA was prepared according to the procedure described in Example A2. About 10 μg each of the chromosomal DNA samples was digested with EcoRI, followed by agarose gel electrophoresis, then blotted on a Hybond-N+ membrane (Amersham International) according to the procedure described in Molecular Cloning (Ibid.).

This membrane was subjected to the Southern analysis using ECL Direct DNA/RNA Labelling & Detection System (Amersham International), with the about 2 kbp DNA fragment prepared in (1) above used as a probe. The result showed that there was a DNA fragment which hybridized with the probe at about 20 kbp in *Aspergillus japonicus* IFO4408, at about 13 kbp in *Aspergillus aculeatus* IFO31348, at about 4 kbp in *Penicillium roqueforti* IAM7254, at about 10 kbp in *Scopulariopsis brevicaulis* IFO4843, IFO5828, IFO5841, IFO6588, IFO31688 and IFO31915s, at about 2.7 kbp in *Scopulariopsis brevicaulis* var. *glabra* IFO7239, and at about 10 kbp in *Scopulariopsis roseola* IFO7564. This result indicated that a β-fructofuranosidase gene can be isolated from a β-fructofuranosidase-producing fungus by making use of its homology to the nucleotide sequence of SEQ ID No. 2 as shown in the sequence listing.

Example B2
Isolation of β-fructofuranosidase Gene from *Penicillium roqueforti* IAM7254

About 20 μg of chromosomal DNA sample derived from *Penicillium roqueforti* IAM7254 was digested with EcoRI, followed by agarose gel electrophoresis. DNA fragments at about 4 kbp were separated and recovered according to the procedure described in Molecular Cloning (Ibid.).

The recovered DNA fragments of about 4 kbp (about 0.5 μg) were ligated with 1 μg of λgt 10 vector, which had been digested with EcoRI and treated with phosphatase, and packaged using an in vitro packaging kit, GIGAPACK II Gold (Stratagene L.L.C.), then introduced in the *E. coli* NM514 to prepare a library. As a result of plaque hybridization using ECL Direct DNA/RNA Labelling & Detection System (Amersham International) with the about 2 kbp DNA fragment prepared in Example B1 used as a probe, four clones turned out positive in about 25,000 plaques. The positive clones were purified by a second screening to prepare phage DNA, which was then analyzed using restriction enzymes. The result showed that all the clones had an identical EcoRI fragment of about 4 kbp.

The about 4 kbp EcoRI fragment was subdivided into a smaller fragment to select the desired DNA region using restriction enzymes, then subcloned to plasmid vector pUC118 or pUC119. The plasmid DNA was obtained from the subclone according to the standard procedure and sequenced using a fluorescence sequencer, ALFred DNA Sequencer (Pharmacia) as shown in the sequence listing (SEQ ID No. 12). The encoded amino acid sequence was as shown in the sequence listing (SEQ ID No. 11).

Example B3
Isolation of β-fructofuranosidase Gene from *Scopulariopsis brevicaulis* IFO4843

About 20 μg of chromosomal DNA sample derived from *Scopularopsis brevicauis* IFO4843 was digested with EcoRI, followed by agarose gel electrophoresis. DNA fragments at about 10 kbp were separated and recovered according to the procedure described in Molecular Cloning (Ibid.).

The recovered DNA fragments of about 10 kbp (about 0.5 μg) were ligated with 1 μg of λDASH II vector, which had been digested with both of HindIII and EcoRI, and packaged using an in vitro packaging kit, GIGAPACK II Gold (Stratagene L.L.C.), then introduced in *E. coli* XLI-Blue MRA (P2), to prepare a library.

As a result of plaque hybridization using ECL Direct DNA/RNA Labelling & Detection System (Amersham International) with the about 2 kbp DNA fragment prepared in Example B1 used as a probe, three clones turned out positive in about 15,000 plaques. The positive clones were purified by a second screening to prepare phage DNA, which was then analyzed using restriction enzymes. The result showed that all the clones had an identical EcoRI fragment of about 10 kbp.

The about 10 kbp EcoRI fragment was subdivided into a smaller fragment to select the desired DNA region using restriction enzymes, then subcloned to plasmid vector pUC118 or pUC119. The plasmid DNA was obtained from the subclone according to the standard procedure and sequenced using a fluorescence sequencer, ALFred DNA Sequencer (Pharmacia) as shown in the sequence listing (SEQ ID No. 14). The encoded amino acid sequence was as shown in the sequence listing (SEQ ID No. 13).

Example B4
Expression of β-fructofuranosidase Gene Derived from *Penicillium roqueforti* IAM7254 in *Trichoderma viride*

An about 4 kbp EcoRI fragment containing a gene encoding β-fructofuranosidase was prepared from the phage DNA obtained in Example B2. The fragment was inserted into the EcoRI site of plasmid vector pUC118 (plasmid pPRS01).

Figure 2:
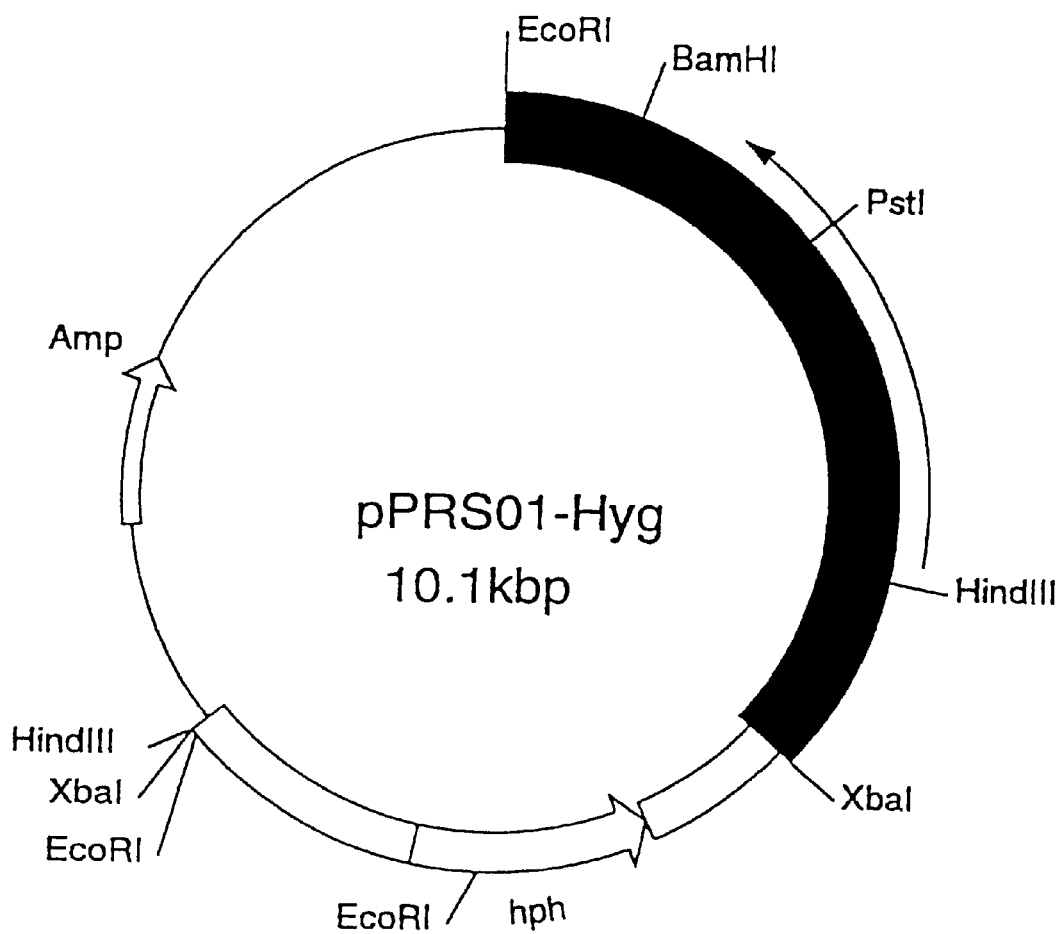
FIG. 2 shows expression vector pPRSO1-Hyg in which a β-fructofuranosidase gene isolated in the process according to the second aspect of the present invention has been introduced.

Further, plasmid pDH25 (D. Cullen et al., (1987) Gene, 57, 21–26) was partially digested with EcoRI and ligated with XbaI linker, and digested again with XbaI. Then, a 3 kbp XbaI fragment which consisted of the promoter and terminator of the trpC gene derived from *Aspergillus nidulans* and hygromycin B phosphotransferase gene derived from *E. coli* was prepared as a hygromycin-resistance gene cassette. The fragment was inserted into the XbaI site of plasmid pPRS01 plasmid pPRS01-Hyg in FIG. 2).

*Trichoderma viride* was cultivated in a seed medium (3% glucose, 0.1% polypepton, 1% yeast extract, 0.14% ammonium sulfate, 0.2% potassium dihydrogenphosphate and 0.03% magnesium sulfate) at 28 C. for 20 hours. The resultant mycelium was collected by centrifugation at 3000 rpm for 10 minutes and washed twice in 0.5 M sucrose solution. The mycelium was suspended in 0.5 M sucrose solution containing 5 mg/ml of Cellularse-Onozuka R-10 (Yakult) and 5 mg/ml of Novozym 234 (Novo Nordisk), and gently shaken at 30° C. for 1 hour to form protoplasts. After the cell body residue was filtered out, the suspensions were centrifuged at 2500 rpm for 10 minutes. The collected protoplasts were washed twice in SUTC buffer solution (0.5 M sucrose, 10 mM Tris-HCl (pH 7.5) and 10 mM calcium chloride) and suspended in the buffer solution to a final concentration of $10^7$/ml.

The protoplast suspension, 100 μl, was mixed with 10 μl of DNA solution, which had been dissolved in TE buffer solution so that the concentration of plasmid pPRS01-Hyg would be 1 mg/ml, and iced for 5 minutes. Then, it was mixed with 400 μl of PEG solution (60% polyethylene glycol 4000, 10 mM Tris-HCl (pH 7.5) and 10 mM calcium chloride), and iced for an additional 20 minutes. Next, the protoplasts were washed in SUTC buffer solution, and laid on a potato dextrose agar medium (Difco) containing 100 μg/ml hygromycin B and 0.5 M sucrose, together with a potato dextrose soft agar medium containing 0.5 M sucrose, and incubated at 28° C. for 5 days. The appeared colonies were selected as transformants.

After the transformant and the original strain were cultivated in the seed medium at 28° C. for 4 days, the β-fructofuranosidase activity of the culture supernatant was measured by allowing the enzyme to act on 10 wt % sucrose solution, pH 5.5, at 40° C. The activity was expressed in units, i.e., the quantity of free glucose ($\mu$mol) released in 1 minute. The original strain turned out negative for the activity, while the transformant exhibited about 0.04 units/ml of activity.

The obtained $\beta$-fructofuranosidase was allowed to act on sucrose for 23 hours at 40° C. in a sucrose solution at a concentration of 60 wt %, pH 7.0, containing 4.2 units of enzyme per 1 g of sucrose. After the reaction, the sugar composition in the solution was 1.6% fructose, 16.2% glucose, 42.3% sucrose, 37.3% GF2 and 2.1% GF3.

Example C

Example C1

Preparation of niaD Transformant from *Aspergillus niger* ACE-2-1

Spores of *Aspergillus niger* ACE-2-1 (ATCC20611) were applied to a minimal agar medium (0.2% sodium glutamate, 0.1% dipotassium hydrogenphosphate, 0.05% magnesium sulfate, 0.05% potassium chloride, 0.001% iron sulfate, 3% sucrose and 0.5% agar, pH 5.5) containing 6% chlorates, and maintained at 30° C. After incubation for about 5 days, strains which formed colonies (chlorate-resistant mutants) were selected and planted in a minimal medium which contained glutamates, nitrates or nitrites as the only nitrogen source for the examination of their requirement for nitrogen source. The result showed that some of the chlorate-resistant mutants (niaD mutant candidates) were able to grow in the minimal medium containing glutamates or nitrites as the only nitrogen source, but not in the one containing nitrates.

Three strains of the niaD mutant candidates were analyzed for the activity of nitrate reductase, which was supposed to be produced by niaD gene, in the cell body. The three strains were cultivated in a liquid medium (0.2% sodium glutamate, 0.1% dipotassium hydrogenphosphate, 0.05% magnesium sulfate, 0.05% potassium chloride, 0.001% iron sulfate and 3% sucrose 3 g) at 30° C. for 60 hours while shaking. The resultant wet cell bodies, 0.2 g, were suspended in 2 ml of 50 mM sodium phosphate buffer (pH 7.5), homogenized, and ultrasonically crushed, then centrifuged to remove the insoluble fraction. The supernatant, 50 $\mu$l, was mixed with 1000 $\mu$l of distilled water, 750 $\mu$l of 0.2 M sodium phosphate solution (pH 7.5), 100 $\mu$l of 0.04 mg/ml FAD, 100 $\mu$l of 2 mg/ml NADPH and 1000 $\mu$l of 22.5 mg/ml sodium nitrate, and allowed to react at 37° C. After reaction was over, the sample solution was colored by the addition of 500 $\mu$l of 1% sulfanilamide (dissolved in 3 N hydrochloric acid) and 500 $\mu$l of 0.02% N-1-naphthylethylenediamine, and measured for A540 for the determination of the nitrate reductase activity. However, these three strains did not exhibit nitrate reductase activity. Therefore, it was concluded that the three strains were niaD mutants, one of which, named NIA5292 strain, was used as a sample in the subsequent experiments.

Example C2

Preparation of niaD Gene from *Aspergillus niger* NRRIA337

(1) Preparation of probe

*Aspergillus niger* NRRIA337 was cultivated in a YPD liquid medium (1% yeast extract, 2% polypepton and 2% glucose). Further, synthetic DNA primers as shown in the sequence listing (SEQ ID Nos. 17 and 18) were prepared by referring to the nucleotide sequence of niaD gene derived from *Aspergillus niger* (Unkles, S. E., et al., Gene 111, 149–155 (1992)). The chromosomal DNA which had been prepared from the aforementioned cell bodies according to the procedure described in Example A2 was used as a template DNA for PCR reaction. The reaction took place in 100 $\mu$l of sample solution containing 0.5 $\mu$g of chromosomal DNA, 100 pmol each of primers and 2.5U of Taq DNA polymerase (Nippon Gene) at 94° C. for 1 minute, at 50° C. for 2 minutes, and at 72° C. for 2 minutes, for a total of 25 cycles. As a result, an about 800 bp DNA fragment was amplified specifically. Then, the nucleotide sequence of this DNA fragment was analyzed and proved to be identical to the reported nucleotide sequence of the niaD gene of *Aspergillus niger*, showing that the DNA fragment was derived from the niaD gene. This about 800 bp DNA fragment was used as a probe in the subsequent experiments.

(2) Southern analysis of chromosomal DNA from *Aspergillus niger*

The chromosomal DNA of *Aspergillus niger* NRRIA337 was digested completely with HindIII, EcoRI and BamHI, followed by electrophoretic fractionation on agarose gel, then blotted on a nylon membrane (Hybond-N+, Amersham International) according to the procedure described in Molecular Cloning (Cold Spring Harbour, 1982). This nylon membrane subjected to Southern analysis using ECL Direct DNA Labelling & Detection System (Amersham International) under the conditions specified in the supplied manual, with the aforementioned about 800 bp DNA fragment used as a probe. As a result, a DNA fragment of about 15 kbp digested with HindIII hybridized with the probe.

(3) Isolation of niaD gene

The chromosomal DNA of the *Aspergillus niger* NRRIA337 was digested completely with HindIII, followed by electrophoretic fractionation on agarose gel. DNA fragments at about 15 kbp were separated and recovered according to the standard procedure. The recovered DNA fragments were ligated with the HindIII site of $\lambda$DASH II, and packaged using GIGAPACK II Gold (Stratagene L.L.C.), then introduced in *E. coli*, to prepare a library.

As a result of plaque hybridization using ECL Direct DNA Labelling & Detection System (Amersham International) with the about 800 bp DNA fragment above used as a probe, positive clones were obtained. The positive clones were purified by a second screening.

Figure 3:
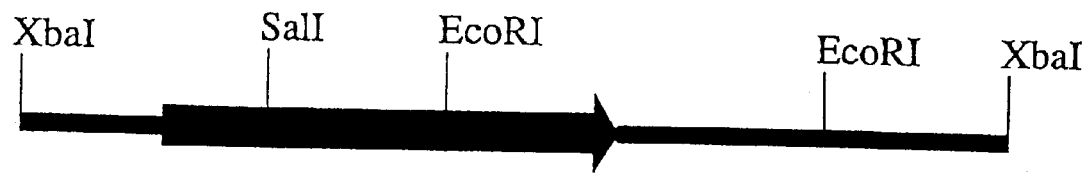
FIG. 3 is the restriction map of a DNA fragment comprising the niaD gene which has been derived from the *Aspergillus niger* NRRL 4337.

Phage DNA prepared from the positive clones were tested positive for a HindIII inserted fragment of about 15 kbp. As a result of Southern Analysis for this inserted fragment, a smaller DNA fragment of about 6.5 kbp containing the niaD gene (XbaI fragment) was found. A restriction enzyme map was determined for this fragment. Then, the XbaI fragment was subdivided into smaller fragments using restriction enzymes, and subcloned to plasmid pUC118. Using the subcloned plasmids as templates, the fragments were sequenced to determine the location of the niaD gene in the isolated DNA fragment (FIG. 3).

Example C3

Construction of Plasmid pAN203 for Gene Targeting

Figure 4A:
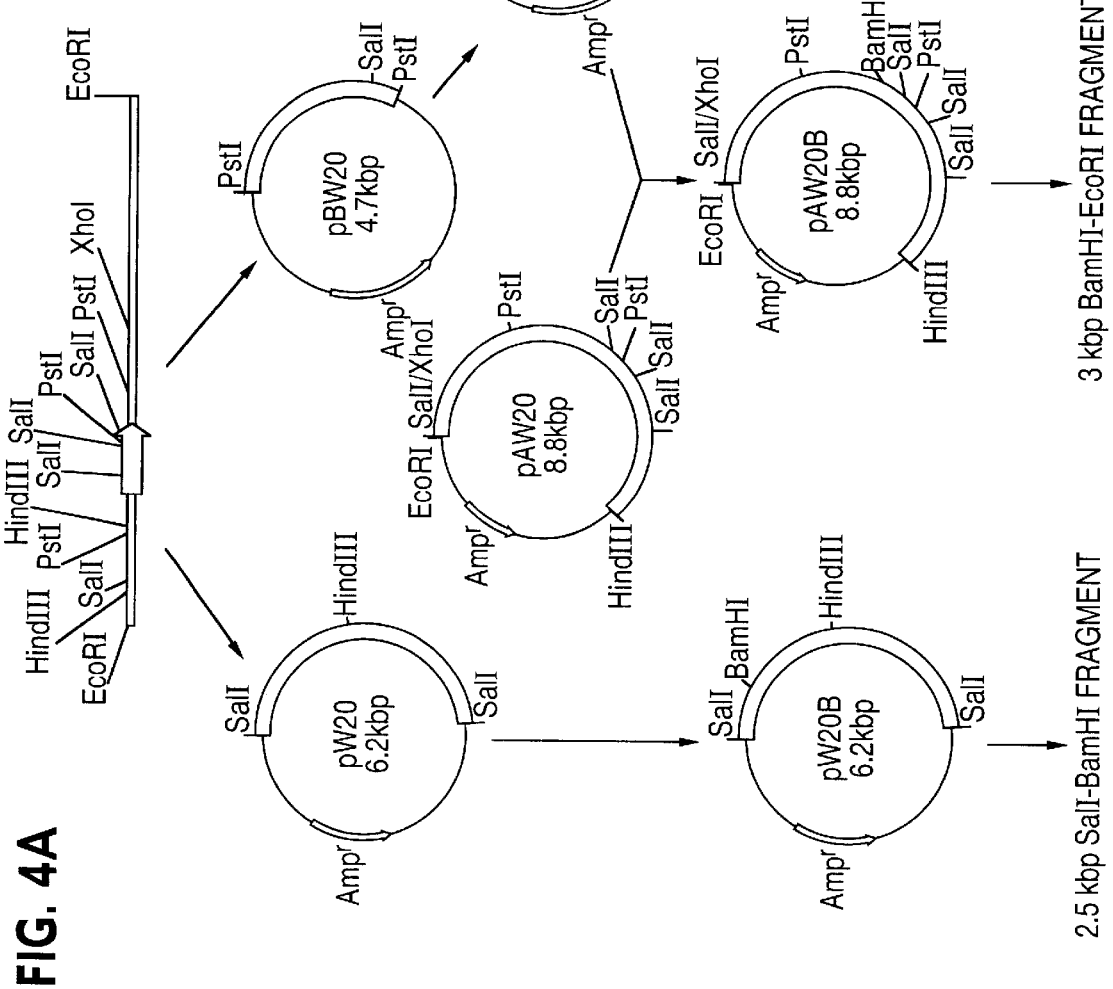
FIGS. 4A and 4B shows the construction of plasmid pAN203.
Figure 4B:
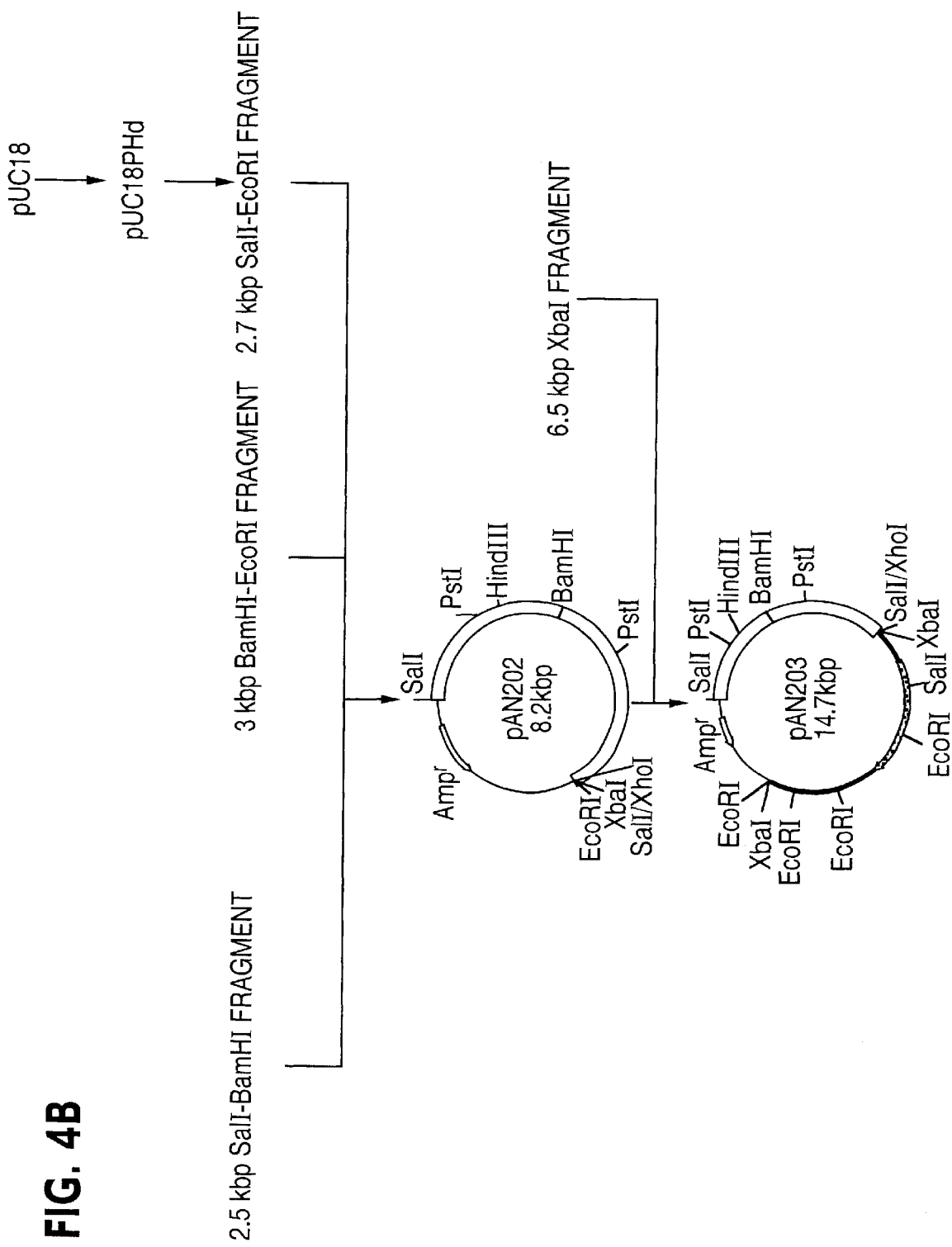

Plasmid pAN203 for gene targeting was constructed as follows (FIG. 4):

An about 3 kbp SalI fragment including the initiation codon of the $\beta$-fructofuranosidase gene and its upstream region was prepared from the about 15 kbp EcoRI fragment containing a $\beta$-fructofuranosidase gene, which had been obtained in Example A3 above, and subcloned to plasmid PUC119 (plasmid pW20). Single-stranded DNA was prepared from this plasmid, and site-specifically mutated using the synthetic DNA of SEQ ID No. 19 as shown in the sequence listing and Sculptor In Vitro Mutagenesis System (Amersham International), to create a BamHI-digestible site immediately before the initiation codon of the $\beta$-fructofuranosidase gene (pW20B).

Further, an about 1.5 kbp PstI fragment containing the termination codon of the β-fructofuranosidase gene and its downstream region was prepared from an about 15 kbp EcoRI fragment containing the β-fructofuranosidase gene, and subcloned to plasmid pUC119 (plasmid pBW20). Single-stranded DNA was prepared from this plasmid, and site-specifically mutated using the synthetic DNA of SEQ ID No. 20 as shown in the sequence listing and Sculptor In Vitro Mutagenesis System (Amersham International), to create a BamHI-digestible site immediately after the termination codon of the β-fructofuranosidase gene (pBW20B). An about 1.5 kbp PstI fragment was prepared from pBW20B and substituted for the about 1.5 kbp PstI fragment of pAW20, which had been prepared in Example A4 (plasmid pAW20B).

Next, plasmid pUC118 was digested with HindIII and, after its terminals were blunted with T4 DNA polymerase takara Shuzo Co., Ltd.), ligated with SalI linker. The DNA was digested with SalI and ligated again (plasmid pUC18PHd). Plasmid pUC18PHd was digested with SalI and EcoRI, and ligated with an about 2.5 kbp SalI-BamHI fragment prepared from pW20B and an about 3 kbp BamHI-EcoRI fragment prepared from pAW20B (plasmid pAN202). Further, an about 6.5 kbp XbaI fragment (FIG. 3) containing the niaD gene was inserted into the XbaI site of pAN202 (plasmid pAN203).

Example C4
Transformation of *Aspergillus niger* NIA5292 with Plasmid pAN203

*Aspergillus niger* NIA5292 was cultivated in a liquid medium (2% soluble starch, 1% polypepton, 0.2% yeast extract, 0.5% sodium dihydrogenphosphate and 0.05% magnesium sulfate) at 28° C. for 24 hours with shaking. The cell bodies were collected with a glass filter, suspended in an enzyme solution (1 mg/ml β-glucuronidase (Sigma Chemical Co.), 5 mg/ml Novozym 234 (Novo Nordisk), 10 mM sodium phosphate (pH 5.8) and 0.8M potassium chloride), and maintained at 30° C. for 1.5 hours. After the cell debris was removed by a glass filter, and the resultant protoplasts were collected by centrifigation. The protoplasts were washed twice in STC buffer (10 mM Tris (H 7.5), 10 mM calcium chloride and 1.2 M sorbitol), and suspended in STC buffer. Next, the protoplasts were mixed with plasmid pAN203 which had been digested with HindIII, and maintained still on ice for 20 minutes. After PEG solution (10 mM Tris (pH 7.5), 10 mM calcium chloride and 60% polyethylene glycol 6000) was added, the sample was maintained still on ice for another 20 minutes. The protoplasts were washed a few times in STC buffer, and suspended in Czapek's medium (0.2% sodium nitrate, 0.1% dipotassium hydrogenphosphate, 0.05% magnesium sulfate, 0.05% potassium chloride, 0.001% ferric sulfate and 3% sucrose) containing 1.2 M sorbitol and 0.8% agar. It was then overlaid on Czapek's agar medium containing 1.2 M sorbitol and 1.5% agar, and incubated at 30° C. After incubation for about 5 days, strains which formed colonies (transformants) were selected and cultivated in a liquid medium. The chromosomal DNAs of the transtormants were extracted and analyzed by the Southern method, in order to select transformant in which only one copy of plasmid pAN203 was inserted by homologous recombination in the upstream region of the host β-fructofuranosidase gene.

Next, the conidia of the transformant were applied to a minimal agar medium (0.2% sodium glutamate, 0.1% dipotassium hydrogenphosphate, 0.05% magnesium sulfate, 0.05% potassium chloride, 0.001% iron sulfate, 2% glucose, 6% potassium chlorate and 1.5% agar, pH 5.5) which contained 6% potassium chlorate and 2% glucose as the only carbon source, and incubated at 30° C. About four days later, a number of chlorate-resistant niaD⁻ phenotype mutants emerged. About half of the chlorate-resistant mutants were tested negatively for β-fructofuranosidase activity, suggesting that the β-fructofuranosidase gene was missing together with the vector bearing the niaD gene as a result of a secondary homologous recombination in the downstream region of the β-fructofuranosidase gene on the host chromosome. The result of Southern Analysis for the chromosomal DNA extracted from the chlorate-resistant mutants (one of which was named NIA1602) confirmed that the β-fructofuranosidase gene and the vector bearing the niaD gene were missing in the chromosome.

Figure 5A:
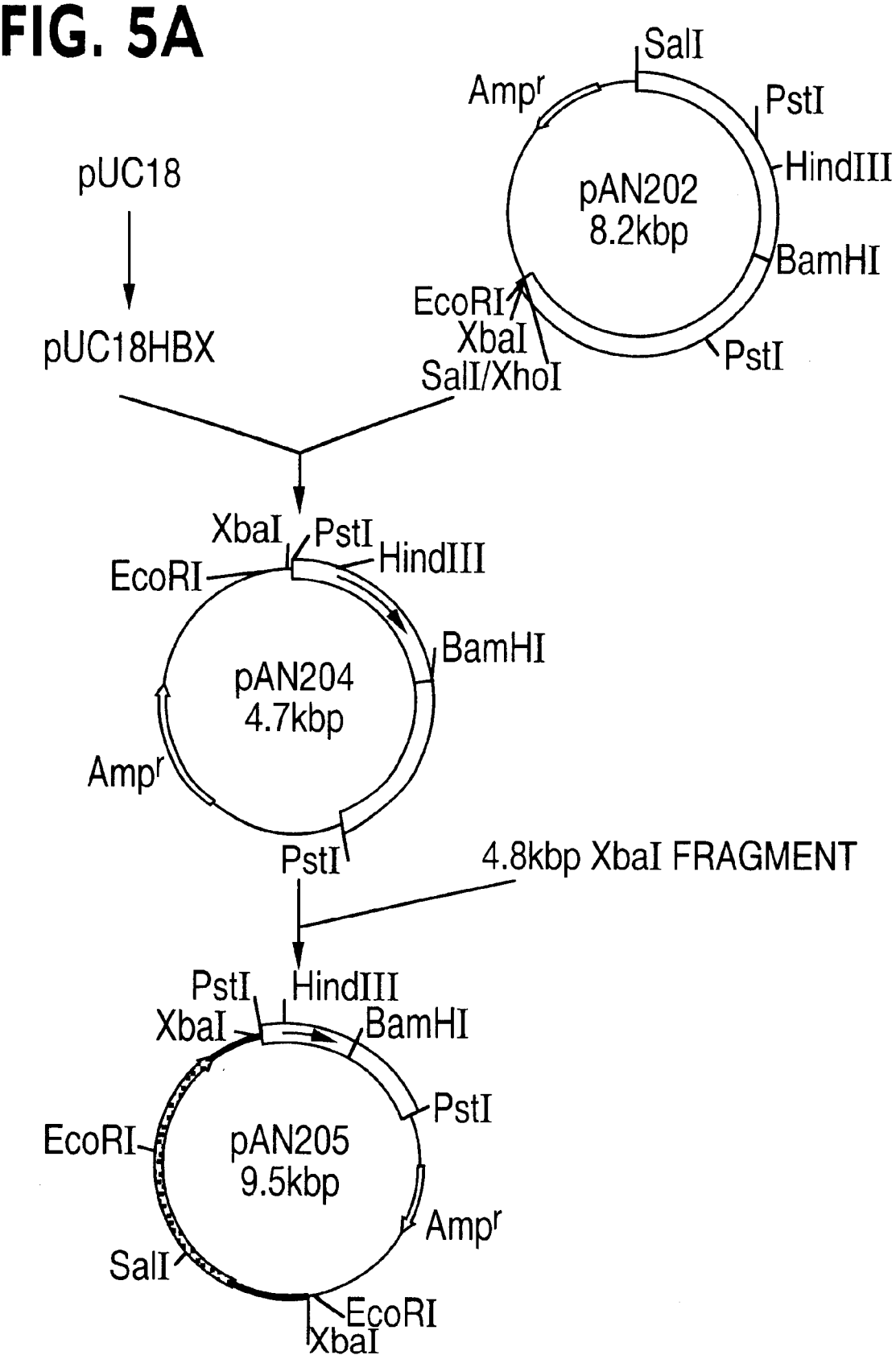
FIGS. 5A and 5B shows the construction of plasmid pAN572.
Figure 5B:
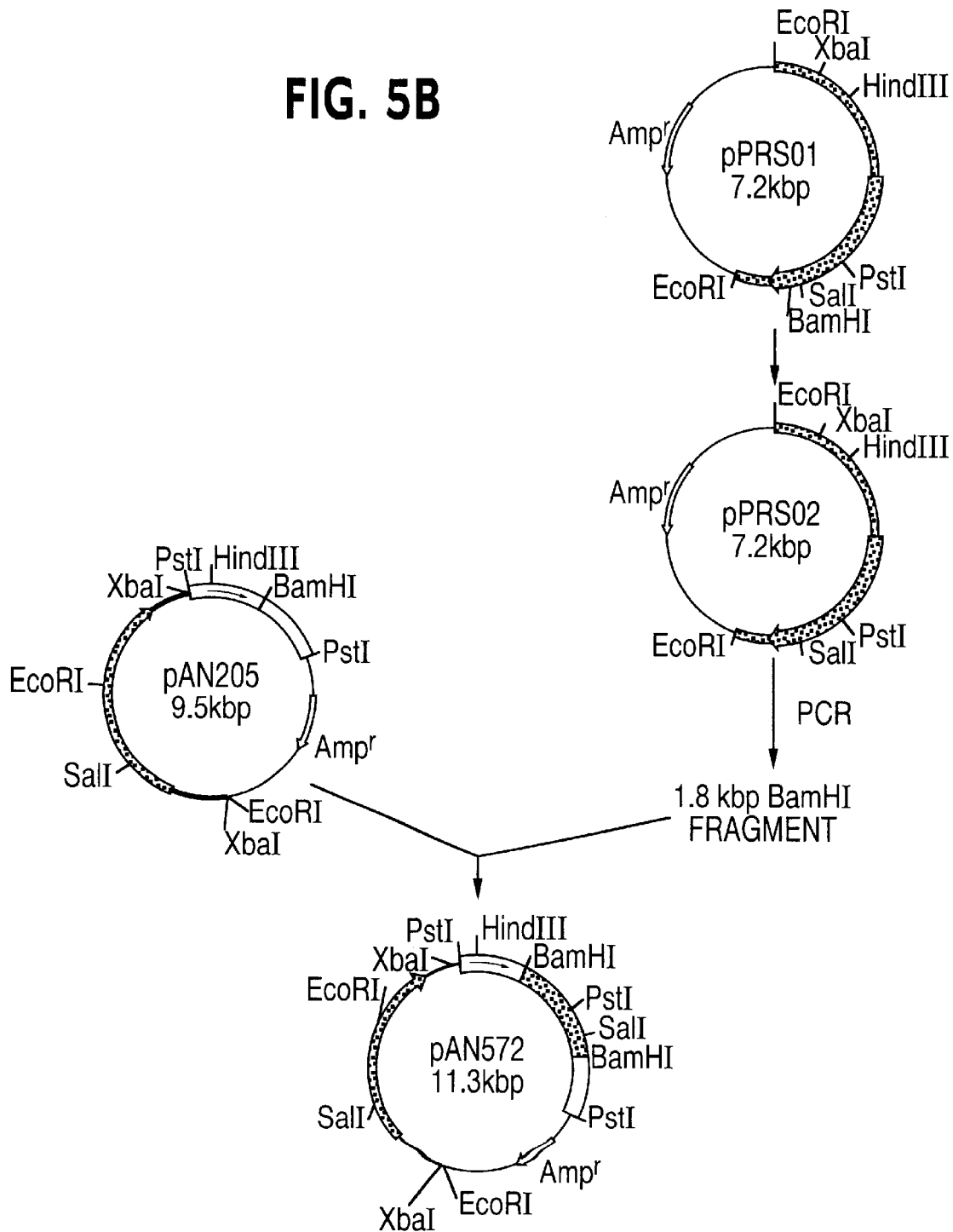

Example C5
Production of β-fructofuranosidase Derived from *Penicillium roqueforti* in *Aspergillus niger* NIA1602 Host To express the β-fructofuranosidase gene derived from *Penicillium roqueforti*, plasmid pAN572 was constructed as follows (FIG. 5): First, plasmid pUC18 was digested with HindIII and, after its terminals were blunted with T4 DNA polymerase Takara Shuzo Co., Ltd.), ligated again. Then, the plasmid was digested with BamHI and, after its terminals were blunted by T4 DNA polymerase, ligated again (plasmid pUC18HBX). An about 2 kbp PstI fragment containing the promoter and terminator of the β-fructofuranosidase gene prepared from plasmid pAN202 was inserted into the PstI site of plasmid pUC18HBX (plasmid pAN204).

Next, in order to make a smaller DNA fragment of the niaD gene and disrupt the BamHI-digestible site, the gene was site-specifically mutated using the synthetic DNA of SEQ ID Nos. 21 and 22 as shown in the sequence listing as primers and Sculptor In Vitro Mutagenesis System (Amersham International). As a result, the BamHI-digestible site was disrupted and an XbaI-digestible site was created on the downstream of the niaD gene, allowing the niaD gene to be prepared as an about 4.8 kbp XbaI fragment without a BamHI-digestible site. This 4.8 kbp XbaI fragment was inserted into the XbaI site of plasmid pAN204 (plasmid pAN205).

Further, the translated region of the β-fructofuranosidase gene derived from *Penicillium roqueforti* was site-specifically mutated to disrupt the BamHI site without changing the encoded amino acid sequence (pPRS02). Mutation took place on Sculptor In Vitro Mutagenesis System (Amersham International), with the single-stranded DNA which had been prepared in Example B4 from plasmid pPRS01 containing the gene used as a template, and the synthetic DNA of SEQ ID No. 23 as shown in the sequence listing used as a primer. Then, an about 1.8 kbp BamHI fragment was prepared from the translated region of the β-fructofuranosidase gene by PCR using the synthetic DNA of SEQ ID No.24 and 25 as shown in the sequence listing as primers and plasmid pPRS02 as template, and inserted into the BamHI site of plasmid pAN205 (plasmid pAN572).

*Aspergillus niger* NIA1602 was transformed according to the procedure described in Example C4 by using plasmid pAN572 which had been digested with HindIII to linearize. One of the transformants was cultivated in a liquid medium (5.0% sucrose, 0.7% malt extract, 1.0% polypepton, 0.5% carboxymethyl cellulose and 0.3% sodium chloride) at 28° C. for 3 days. After cultivation, the recovered cell bodies were ultrasonically homogenized, and measured for β-fructofuranosidase activity in units, i.e., the quantity of free glucose ($\mu$mol) released in 1 minute in 10 wt % sucrose solution, pH 5.5, at 40° C. The transformant exhibited $1 \times 10^{-3}$ units/ml of activity.

Example D

For ease of reference, a β-fructofuranosidase variant is hereinafter denoted by the following:

Original amino acid/position/Substitutional amino acid

According to this, for example, a variant in which tryptophan is substituted for phenylalanine at position 170 is expressed as "F170W."

A variant with more than one mutation is denoted by a series of mutation symbols separated by a '+', such as in:

F170W+G300V+H313K where tryptophan, valine and lysine are substituted for phenylalanine, glycine and histidine at positions 170, 300 and 313, respectively.

Further, fructose, glucose and sucrose are hereinafter denoted by 'F', 'G', 'GF', respectively, while oligosaccharides in which one to three molecules of fructose are coupled with sucrose are denoted by 'GF2', 'GF3', and 'GF4', respectively.

Figure 6:
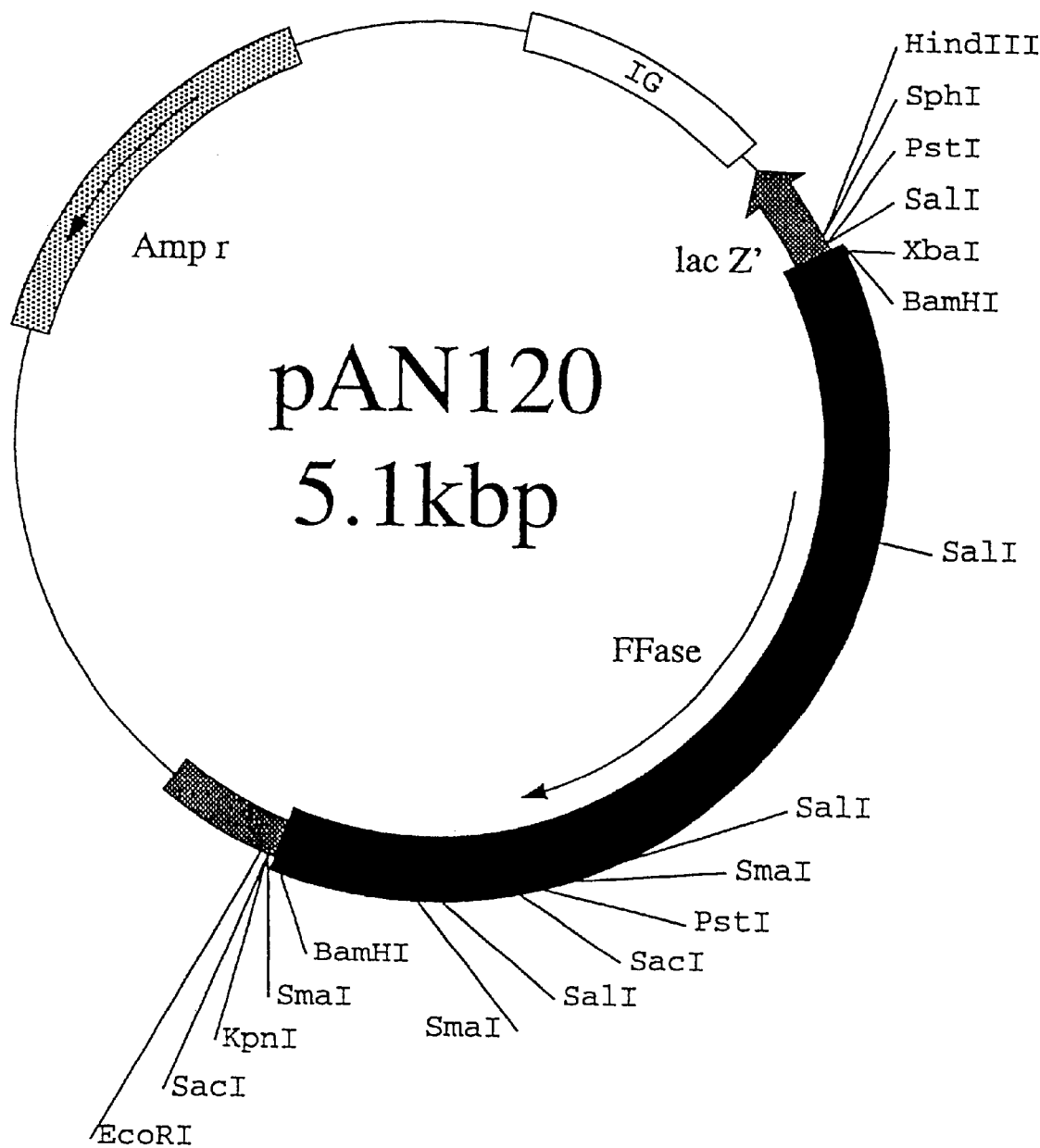
FIG. 6 is the restriction map of plasmid pAN120.

Example D1
Construction and Production of F170W Variant (1) Nucleotide substitution in β-fructofuranosidase gene by site-specific mutation The translated region of the β-fructofuranosidase gene derived from *Aspergillus niger* ACE-2-1 (ATCC20611) was amplified by PCR using Perkin Elmer Cetus DNA Thermal Cycler, with plasmid pAW20-Hyg (see Example A4) containing the β-fructofuranosidase gene used as template DNA. The sample solution contained 0.5 µl (equivalent to 0.1 µg) of plasmid DNA (pAW20-Hyg), 10 µl of reaction buffer solution [500 mM KCl, 100 mM Tris-HCl (pH 8.3), 15 mM $MgCl_2$ and 1% Triton X-100], 8 µl of 2.5 mM dNTP solution, 2 µl each of 0.01 mM positive-chain DNA primer of SEQ ID No. 26 as shown in the sequence listing (primer #1) and negative-chain DNA primer of SEQ ID No. 27 as shown in the sequence listing (primer #2), 0.5 µl Taq DNA polymerase (Wako Pure Chemical Industries, Ltd.), and 77 µl of sterilized water, with a total volume of 100 µl. After pretreatment at 94° C. for 5 minutes, the sample was incubated at 94° C. for 1 minute (degeneration step), at 54° C. for 2 minutes (annealing step), and at 72° C. for 3 minutes (extending step), for a total of 25 reaction cycles. The last cycle was followed by incubation at 72° C. for 7 minutes. The sample was then extracted with a mixture of phenol, chloroform and isoamyl alcohol, and allowed to sediment in ethanol. The precipitate was dissolved in 20 µl of TE buffer solution and electrophoresed through agarose gel. The specifically amplified band at about 2 kbp was cut out using the standard technique. The recovered DNA fragment was digested with BamHI, then inserted into the BamHI site of plasmid pUC118 (Takara Shuzo Co., Ltd.) (plasmid pAN120 in FIG. 6).

Plasmid pAN120 was introduced in the *E. coil* CJ236 strain to prepare single-stranded DNA according to the standard procedure. With the obtained DNA used as a template and the DNA primer of SEQ ID No. 28 as shown in the sequence listing as a primer, a site specific mutation was induced by using Muta-Gene In Vitro Mutagenesis Kit (Nihon Bio-Rad Laboratories) according to the instructions given in the supplied manual (plasmid pAN 120 (F170W)).

The result of sequencing for the inserted fragment of pAN120 (F170W) confirmed that substitution occurred only in the target nucleotide and no other part of the sequence. In other words, the a β-fructofuranosidase encoded by the variant gene was the same as the original enzyme except that tryptophan was substituted for phenylalanine at position 170.

(2) Construction of expression vector pY2831 for use in yeast

Figure 7:
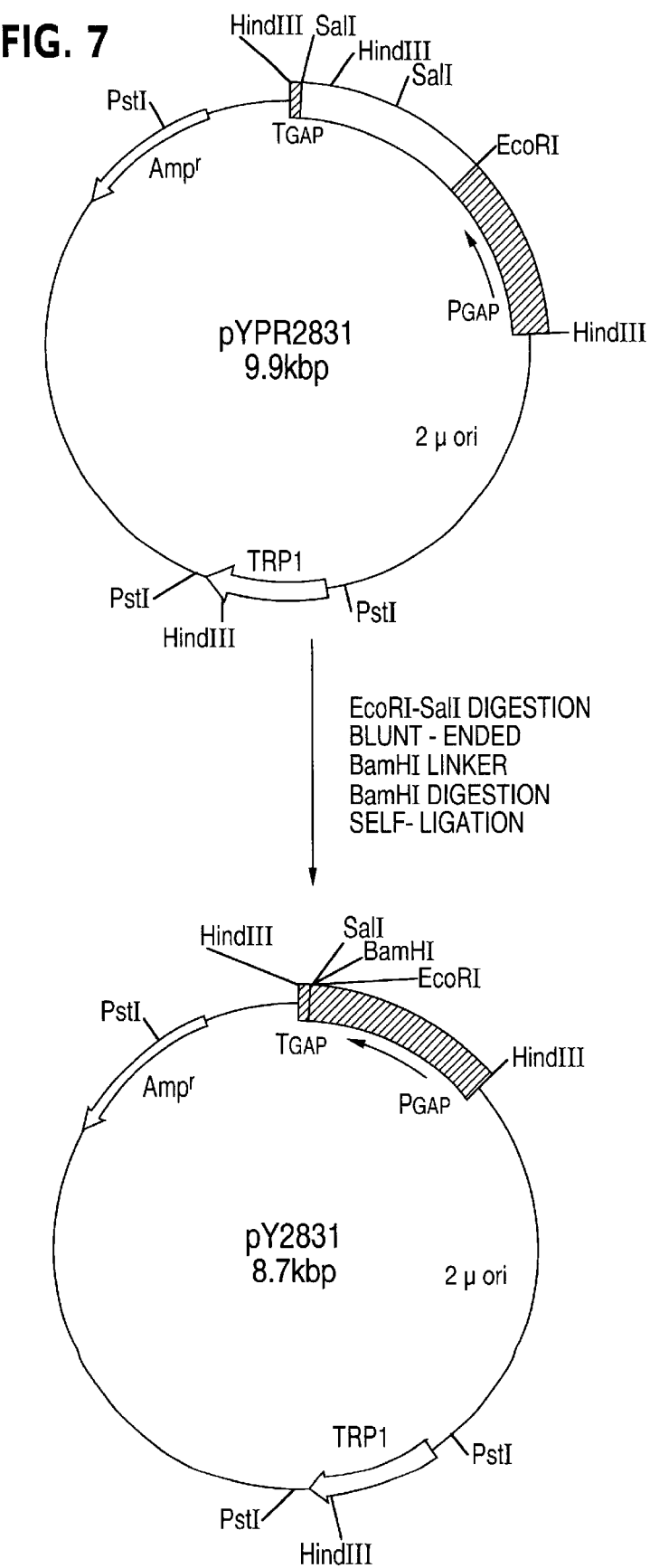
FIG. 7 shows the construction of plasmid pY2831.

Expression vector pY2831 for use in yeast was prepared from plasmid pYPR2831 (H. Horiuchi et al., Agric. Biol. Chem., 54, 1771–1779, 1990). As shown in FIG. 7, the plasmid was first digested with EcoRI and SalI and, after its terminals were blunted with T4DNA polymerase, ligated with BamHI linker (5'-CGGATCCG-3'), then digested again with BamHI and finally self-ligated (plasmid pY2831).

(3) Production of variant F170W by yeast

Figure 8:
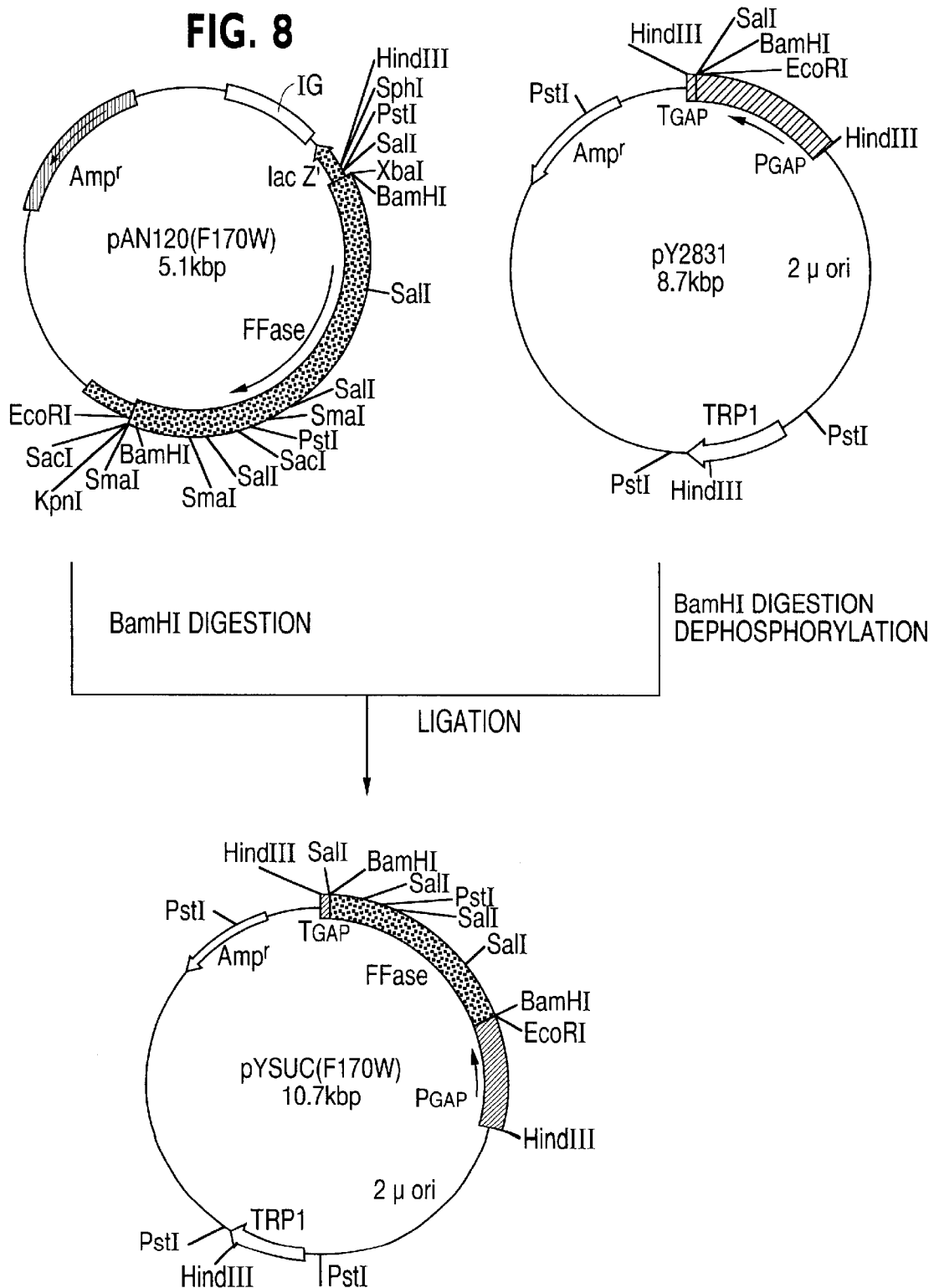
FIG. 8 shows the construction of plasmid pYSUC (F170W).

A 2 kbp BamHI DNA fragment including the variant gene was prepared from plasmid pAN 120 (F 170W) by digesting it with BamHI, and inserted into the BamHI site of pY2831 (plasmid pYSUC (F170W) in FIG. 8). A plasmid for expressing the wild type enzyme (plasmid pYSUC) was constructed in a similar manner from Plasmid pAN120.

These plasmids were introduced in the yeast *Saccharomyces cerevisiae* MS-161 (Suc⁻, ura3, trp1) by the lithium acetate method Ito, H. et al., J. Bacteriol., 153, 163–168, 1983) to prepare a transformant. The transformant was cultivated overnight in an SD-Ura medium (0.67% yeast nitrogen base (Difco), 2% glucose and 50 µg/ml uracil) at 30° C. The culture was seeded in a production medium (0.67% yeast nitrogen base (Difco), 2% glucose, 2% casamino acids and 50 µg/ml uracil) at a final concentration of 1% and cultivated at 30° C. for 2 days. The culture supernatant was measured for β-fructofuranosidase activity according to the procedure described in Agric. Biol. Chem., 53, 667–673 (1989). The activity was 12.7 units/ml in the wild type enzyme, and 10.1 units/ml in the F170W variant.

(4) Evaluation of variant F170W

The wild type enzyme and the variant F170W were evaluated using the yeast culture supernatant. After reaction in a 48 wt % sucrose solution, pH 7, at 40° C., the sugar composition was analyzed by HPLC. The sugar compositions (%) for the wild type and the variant when 1-kestose (GF2) yield was at maximum were as follows:

|  | F | G | GF | GF2 | GF3 | GF4 |
|---|---|---|---|---|---|---|
| Wild type | 0.4 | 22.3 | 20.5 | 45.1 | 11.3 | 0.3 |
| F170W | 0.6 | 22.1 | 20.9 | 45.8 | 10.3 | 0.3 |

These figures indicate that GF2 increases and GF3 decreases as a result of the substitution in F170W.

Example D2
Construction and Production of Variant G300W (1) Nucleotide substitution in β-fructofuranosidase gene by site-specific mutation A site specific mutation was induced in the same manner as in Example D1 except that the DNA primer of SEQ ID No. 29 as shown in the sequence listing was used to construct plasmid pAN120 (G300W).

The result of sequencing for the inserted fragment of pAN120 (G300W) confirmed that substitution occurred only in the target nucleotide and no other part of the sequence. In other words, the β-fructofuranosidase encoded by the variant gene was the same as the original enzyme except that tryptophan was substituted for glycine at position 300.

(2) Production of variant G300W by yeast

A 2 kbp BamHI DNA fragment including the variant gene was prepared from plasmid pAN120 (G300W) by digesting it with BamHI, and inserted into the BamHI site of pY2831 (plasmid pYSUC (G300W)).

Plasmid pYSUC (G300W) was introduced in the yeast *Saccharomyces cerevisiae* MS-161 in the same manner as in Example D1 to produce variant G300W. The culture supernatant exhibited a β-fructofuranosidase activity of 5.0 units/ml.

(3) Evaluation of variant G300W

The wild type enzyme and the variant G300W were evaluated using the yeast culture supernatant. After reaction in a 48 wt % sucrose solution, pH 7, at 40° C., the sugar composition was analyzed by HPLC. The sugar compositions (%) for the wild type and the variant when 1-kestose (GF2) yield was at maximum were as follows:

|  | F | G | GF | GF2 | GF3 | GF4 |
| --- | --- | --- | --- | --- | --- | --- |
| Wild type | 0.4 | 22.3 | 20.5 | 45.1 | 11.3 | 0.3 |
| G300W | 0.6 | 21.9 | 21.7 | 46.4 | 9.4 | 0.0 |

These figures indicate that GF2 increases and GF3 decreases as a result of the substitution in G300W.

Example D3
Construction and Production of Variant H313K (1) Nucleotide substitution in β-fructofuranosidase gene by site-specific mutation A site specific mutation was induced in the same manner as in Example D1 except that the DNA primer of SEQ ID No. 30 as shown in the sequence listing was used to construct plasmid pAN120 (H313K).

The result of sequencing for the inserted fragment of pAN120 (H313K) confirmed that substitution occurred only in the target nucleotide and no other part of the sequence. In other words, the β-fructofuranosidase encoded by the variant gene was the same as the original enzyme except that lysine was substituted for histidine at position 313.

(2) Production of variant H313K by yeast

A 2 kbp BamHI DNA fragment including the variant gene was prepared from plasmid pAN120 (H313K) by digesting it with BamHI, and inserted into the BamHI site of pY2831 (plasmid pYSUC (H313K)).

Plasmid pYSUC (H313K) was introduced in the yeast *Saccharomyces cerevisiae* MS-161 in the same manner as in Example D1 to produce variant H313K. The culture supernatant exhibited a β-fructofuranosidase activity of 5.0 units/ml.

(3) Evaluation of variant H313K The wild type enzyme and the variant H313K were evaluated using the yeast culture supernatant. After reaction in a 48 wt % sucrose solution, pH 7, at 40° C., the sugar composition was analyzed by HPLC. The sugar compositions (%) for the wild type and the variant when 1-kestose (GF2) yield was at maximum were as follows:

|  | F | G | GF | GF2 | GF3 | GF4 |
| --- | --- | --- | --- | --- | --- | --- |
| Wild type | 0.4 | 22.3 | 20.5 | 45.1 | 11.3 | 0.3 |
| H313K | 0.4 | 21.9 | 18.8 | 52.9 | 6.0 | 0.0 |

These figures indicate that GF2 increases and GF3 decreases as a result of the substitution in H313K.

Example D4
Construction and Production of Variant E386K (1) Nucleotide substitution in β-fructofuranosidase gene by site-specific mutation A site specific mutation was induced in the same manner as in Example D1 except that the DNA primer of SEQ ID No. 31 as shown in the sequence listing was used to construct plasmid pAN120 (E386K).

The result of sequencing for the inserted fragment of pAN120 (E386K) confirmed that substitution occurred only in the target nucleotide and no other part of the sequence. In other words, the β-fructofuranosidase encoded by the variant gene was the same as the original enzyme except that lysine was substituted for glutamic acid at position 386.

(2) Production of variant E386K by yeast

A 2 kbp BamHI DNA fragment including the variant gene was prepared from plasmid pAN120 (E386K) by digesting it with BamHI, and inserted into the BamHI site of pY2831 (plasmid pYSUC (E386K)).

Plasmid pYSUC (E386K) was introduced in the yeast *Saccharomyces cerevisiae* MS-161 in the same manner as in Example D1 to produce variant E386K. The culture supernatant exhibited a β-fructofuranosidase activity of 10.7 units/ml.

(3) Evaluation of variant E386K

The wild type enzyme and the variant E386K were evaluated using the yeast culture supernatant. After reaction in a 48 wt % sucrose solution, pH 7, at 40° C., the sugar composition was analyzed by HPLC. The sugar compositions (%) for the wild type and the variant when 1-kestose (GF2) yield was at maximum were as follows:

|  | F | G | GF | GF2 | GF3 | GF4 |
| --- | --- | --- | --- | --- | --- | --- |
| Wild type | 0.4 | 22.3 | 20.5 | 45.1 | 11.3 | 0.3 |
| E386K | 22.3 | (F + G) | 19.9 | 49.3 | 7.9 | 0.6 |

These figures indicate that GF2 increases and GF3 decreases as a result of the substitution in E386K.

Example D5
Construction and Production of Variant F170W+G300W (1) Nucleotide substitution in β-fructofuranosidase gene by site-specific mutation Site specific mutations were induced in the same manner as in Example D1 except that the DNA primers of SEQ ID Nos. 28 and 29 as shown in the sequence listing were used to construct plasmid pAN120 (F170W+G300W).

The result of sequencing for the inserted fragment of pAN120 (F170W+G300W) confirmed that substitution occurred only in the target nucleotides and no other part of the sequence. In other words, the β-fructofuranosidase encoded by the variant gene was the same as the original enzyme except that tryptophan was substituted for phenylalanine at position 170 and glycine at position 300.

(2) Production of variant F170W+G300W by yeast

A 2 kbp BamHI DNA fragment including the variant gene was prepared from plasmid pAN120 (F170W+G300W) by digesting it with BamHI, and inserted into the BamHI site of pY2831 (plasmid pYSUC (F170W+G300W)).

Plasmid pYSUC (F170W+G300W) was introduced in the yeast *Saccharomyces cerevisiae* MS-161 in the same manner as in Example D1 to produce variant F170W+G300W. The culture supernatant exhibited a β-fructofuranosidase activity of 2.3 units/ml.

(3) Evaluation of variant F170W+G300W

The wild type enzyme and the variant F170W+G300W were evaluated using the yeast culture supernatant. After reaction in a 48 wt % sucrose solution, pH 7, at 40° C., the sugar composition was analyzed by HPLC. The sugar compositions (%) for the wild type and the variant when 1-kestose (GF2) yield was at maximum were as follows:

|  | F | G | GF | GF2 | GF3 | GF4 |
| --- | --- | --- | --- | --- | --- | --- |
| Wild type | 0.4 | 22.3 | 20.5 | 45.1 | 11.3 | 0.3 |
| F170W + G300W | 0.7 | 21.7 | 22.5 | 46.7 | 8.0 | 0.3 |

These figures indicate that GF2 increases and GF3 decreases as a result of the substitution in F170W+G300W.

Example D6

Construction and Production of Variant F170W+G300W+H313R (1) Nucleotide substitution in β-fructofuranosidase gene by site-specific mutation Site specific mutations were induced in the same manner as in Example D1 except that the DNA primers of SEQ ID Nos. 28, 29 and 32 as shown in the sequence listing were used to construct plasmid pAN 120 (F170W+G300W+H313R).

The result of sequencing for the inserted fragment of pAN120 (F170W+G300W+H313R) confirmed that substitution occurred only in the target nucleotides and no other part of the sequence. In other words, the β-fructofuranosidase encoded by the variant gene was the same as the original enzyme except that tryptophan was substituted for phenylalanine at position 170 and glycine at position 300, and arginine for histidine at position 313.

(2) Production of variant F170W+G300W+H313R by yeast

A 2 kbp BamHI DNA fragment including the variant gene was prepared from plasmid pAN120 (F170W+G300W+H313R) by digesting it with BamHI, and inserted into the BamHI site of pY2831 (plasmid pYSUC (F170W+G300W+H313R)).

Plasmid pYSUC (F170W+G300W+H313R) was introduced in the yeast *Saccharomyces cerevisiae* MS-161 in the same manner as in Example D1 to produce variant F170W+G300W+H313R. The culture supernatant exhibited a β-fructofuranosidase activity of 0.9 units/ml.

(3) Evaluation of variant F170W+G300W+H313R

The wild type enzyme and the variant F170W+G300W+H313R were evaluated using the yeast culture supernatant. After reaction in a 48 wt % sucrose solution, pH 7, at 40° C., the sugar composition was analyzed by HPLC. The sugar compositions (%) for the wild type and the variant when 1-kestose (GF2) yield was at maximum were as follows:

|  | F | G | GF | GF2 | GF3 | GF4 |
| --- | --- | --- | --- | --- | --- | --- |
| Wild type | 0.4 | 22.3 | 20.5 | 45.1 | 11.3 | 0.3 |
| F170W + G300W + H313R | 1.4 | 24.0 | 18.6 | 48.8 | 7.2 | 0.0 |

These figures indicate that GF2 increases and GF3 decreases as a result of the substitution in F170W+G300W+H313R.

Example D7

Construction and Production of Variant G300W+H313K (1) Nucleotide substitution in β-fructofuranosidase gene by site-specific mutation Site specific mutations were induced in the same manner as in Example D1 except that the DNA primers of SEQ ID Nos. 29 and 30 as shown in the sequence listing were used to construct plasmid pAN120 (G300W+H313K).

The result of sequencing for the inserted fragment of pAN120 (G300W+H313K) confirmed that substitution occurred only in the target nucleotides and no other part of the sequence. In other words, the β-fructofuranosidase encoded by the variant gene was the same as the original enzyme except that tryptophan was substituted for glycine at position 300, and lysine for histidine at position 313.

(2) Production of variant G300W+H313K by yeast

A 2 kbp BamHI DNA fragment including the variant gene was prepared from plasmid pAN120 (G300W+H313K) by digesting it with BamHI, and inserted into the BamHI site of pY2831 (plasmid pYSUC (G300W+H313K)).

Plasmid pYSUC (G300W+H313K) was introduced in the yeast *Saccharomyces cerevisiae* MS-161 in the same manner as in Example D1 to produce variant G300W+H313K. The culture supernatant exhibited a β-fructofuranosidase activity of 1.2 units/ml.

(3) Evaluation of variant G300W+H313K

The wild type enzyme and the variant G300W+H313K were evaluated using the yeast culture supernatant. After reaction in a 48 wt % sucrose solution, pH 7, at 40° C., the sugar composition was analyzed by HPLC. The sugar compositions (%) for the wild type and the variant when 1-kestose (GF2) yield was at maximum were as follows:

|  | F | G | GF | GF2 | GF3 | GF4 |
| --- | --- | --- | --- | --- | --- | --- |
| Wild type | 0.4 | 22.3 | 20.5 | 45.1 | 11.3 | 0.3 |
| C300W + H313K | 0.8 | 21.2 | 19.4 | 53.8 | 4.7 | 0.0 |

These figures indicate that GF2 increases and GF3 decreases as a result of the substitution in G300W+H313K.

Example D8

Construction and Production of Variant G300V+H313K (1) Nucleotide substitution in β-fructofuranosidase gene by site-specific mutation Site specific mutations were induced in the same manner as in Example D1 except that the DNA primers of SEQ ID Nos. 30 and 33 as shown in the sequence listing were used to construct plasmid pAN120 (G300V+H313K).

The result of sequencing for the inserted fragment of pAN120 (G300V+H313K) confirmed that substitution occurred only in the target nucleotides and no other part of the sequence. In other words, the β-fructofuranosidase encoded by the variant gene was the same as the original enzyme except that valine was substituted for glycine at position 300, and lysine for histidine at position 313.

(2) Production of variant G300V+H313K by yeast

A 2 kbp BamHI DNA fragment including the variant gene was prepared from plasmid pAN120 (G300V+H313K) by digesting it with BamHI, and inserted into the BamHI site of pY2831 (plasmid pYSUC (G300V+H313K)).

Plasmid pYSUC (G300V+H313K) was introduced in the yeast *Saccharomyces cerevisiae* MS-161 in the same manner as in Example D1 to produce variant G300V+H313K. The culture supernatant exhibited a β-fructofuranosidase activity of 3.6 units/ml.

(3) Evaluation of variant G300V+H313K

The wild type enzyme and the variant G300V+H313K were evaluated using the yeast culture supernatant. After reaction in a 48 wt % sucrose solution, pH 7, at 40° C., the sugar composition was analyzed by HPLC. The sugar compositions (%) for the wild type and the variant when 1-kestose (GF2) yield was at maximum were as follows:

|  | F | G | GF | GF2 | GF3 | GF4 |
|---|---|---|---|---|---|---|
| Wild type | 0.4 | 22.3 | 20.5 | 45.1 | 11.3 | 0.3 |
| G300V + H313K | 0.9 | 21.6 | 19.0 | 53.7 | 4.7 | 0.0 |

These figures indicate that GF2 increases and GF3 decreases as a result of the substitution in G300V+H313K.

Example D9
Construction and Production of Variant G300E+H313K (1) Nucleotide substitution in β-fructofuranosidase gene by site-specific mutation Site specific mutations were induced in the same manner as in Example D1 except that the DNA primers of SEQ ID Nos. 30 and 34 as shown in the sequence listing were used to construct plasmid pAN120 (G300E+H313K).

The result of sequencing for the inserted fragment of pAN120 (G300E+H313K) confirmed that substitution occurred only in the target nucleotides and no other part of the sequence. In other words, the β-fructofuranosidase encoded by the variant gene was the same as the original enzyme except that glutamic acid was substituted for glycine at position 300, and lysine for histidine at position 313.

(2) Production of variant G300E+H313K by yeast

A 2 kbp BamHI DNA fragment including the variant gene was prepared from plasmid pAN120 (G300E+H313K) by digesting it with BamHI, and inserted into the BamHI site of pY2831 (plasmid pYSUC (G300E+H313K)).

Plasmid pYSUC (G300E+H313K) was introduced in the yeast *Saccharomyces cerevisiae* MS-161 in the same manner as in Example D1 to produce variant G300E+H313K. The culture supernatant exhibited a β-fructofuranosidase activity of 2.9 units/ml.

(3) Evaluation of variant G300E+H313K

The wild type enzyme and the variant G300E+H313K were evaluated using the yeast culture supernatant. After reaction in a 48 wt % sucrose solution, pH 7, at 40° C., the sugar composition was analyzed by HPLC. The sugar compositions (%) for the wild type and the variant when 1-kestose (GF2) yield was at maximum were as follows:

|  | F | G | GF | GF2 | GF3 | GF4 |
|---|---|---|---|---|---|---|
| Wild type | 0.4 | 22.3 | 20.5 | 45.1 | 11.3 | 0.3 |
| G300E + H313K | 1.2 | 22.0 | 19.3 | 52.8 | 4.7 | 0.0 |

These figures indicate that GF2 increases and GF3 decreases as a result of the substitution in G300E+H313K.

Example D10
Construction and Production of Variant G300D+H313K (1) Nucleotide substitution in β-fructofuranosidase gene by site-specific mutation Site specific mutations were induced in the same manner as in Example D1 except that the DNA primers of SEQ ID Nos. 30 and 35 as shown in the sequence listing were used to construct plasmid pAN120 (G300D+H313K).

The result of sequencing for the inserted fragment of pAN120 (G300D+H313K) confirmed that substitution occurred only in the target nucleotides and no other part of the sequence. In other words, the β-fructofuranosidase encoded by the variant gene was the same as the original enzyme except that aspartic acid was substituted for glycine at position 300, and lysine for histidine at position 313.

(2) Production of variant G300D+H313K by yeast

A 2 kbp BamHI DNA fragment including the variant gene was prepared from plasmid pAN120 (G300D+H313K) by digesting it with BamHI, and inserted into the BamHI site of pY2831 (plasmid pYSUC (G300D+H313K)).

Plasmid pYSUC (G300D+H313K) was introduced in the yeast *Saccharomyces cerevisiae* MS-161 in the same manner as in Example D1 to produce variant G300D+H313K. The culture supernatant exhibited a β-fructofuranosidase activity of 4.3 units/ml.

(3) Evaluation of variant G300D+H313K

The wild type enzyme and the variant G300D+H313K were evaluated using the yeast culture supernatant. After reaction in a 48 wt % sucrose solution, pH 7, at 40° C., the sugar composition was analyzed by HPLC. The sugar compositions (%) for the wild type and the variant when 1-kestose (GF2) yield was at maximum were as follows:

|  | F | G | GF | GF2 | GF3 | GF4 |
|---|---|---|---|---|---|---|
| Wild type | 0.4 | 22.3 | 20.5 | 45.1 | 11.3 | 0.3 |
| G300D + H313K | 0.5 | 21.6 | 19.6 | 53.3 | 5.0 | 0.0 |

These figures indicate that GF2 increases and GF3 decreases as a result of the substitution in G300D+H313K.

Example D11
Construction and Production of Variant F170W+G300W+H313K (1) Nucleotide substitution in β-fructofuranosidase gene by site-specific mutation Site specific mutations were induced in the same manner as in Example D1 except that the DNA primers of SEQ ID Nos. 28, 29 and 30 as shown in the sequence listing were used to construct plasmid pAN120 (F170W+G300W+H313K).

The result of sequencing for the inserted fragment of pAN120 (F170W+G300W+H313K) confirmed that substitution occurred only in the target nucleotides and no other part of the sequence. In other words, the β-fructofuranosidase encoded by the variant gene was the same as the original enzyme except that tryptophan was substituted for phenylalanine at position 170 and glycine at position 300, and lysine for histidine at position 313.

(2) Production of variant F170W+G300W+H313K by yeast

A 2 kbp BamHI DNA fragment including the variant gene was prepared from plasmid pAN120 (F170W+G300W+H313K) by digesting it with BamHI, and inserted into the BamHI site of pY2831 (plasmid pYSUC (F170W+G300W+H313K)).

Plasmid pYSUC (F170W+G300W+H313K) was introduced in the yeast *Saccharomyces cerevisiae* MS-161 in the same manner as in Example D1 to produce variant F170W+G300W+H313K. The culture supernatant exhibited a β-fructofuranosidase activity of 2.0 units/ml.

(3) Evaluation of variant F170W+G300W+H313K

The wild type enzyme and the variant F170W+G300W+H313K were evaluated using the yeast culture supernatant.

After reaction in a 48 wt % sucrose solution, pH 7, at 40° C., the sugar composition was analyzed by HPLC. The sugar compositions (%) for the wild type and the variant when 1-kestose (GF2) yield was at maximum were as follows:

|  | F | G | GF | GF2 | GF3 | GF4 |
|---|---|---|---|---|---|---|
| Wild type | 0.4 | 22.3 | 20.5 | 45.1 | 11.3 | 0.3 |
| F170W + G300W + H313K | 0.7 | 22.3 | 18.9 | 54.3 | 3.9 | 0.0 |

These figures indicate that GF2 increases and GF3 decreases as a result of the substitution in F170W+G300W+H313K.

Figure 9:
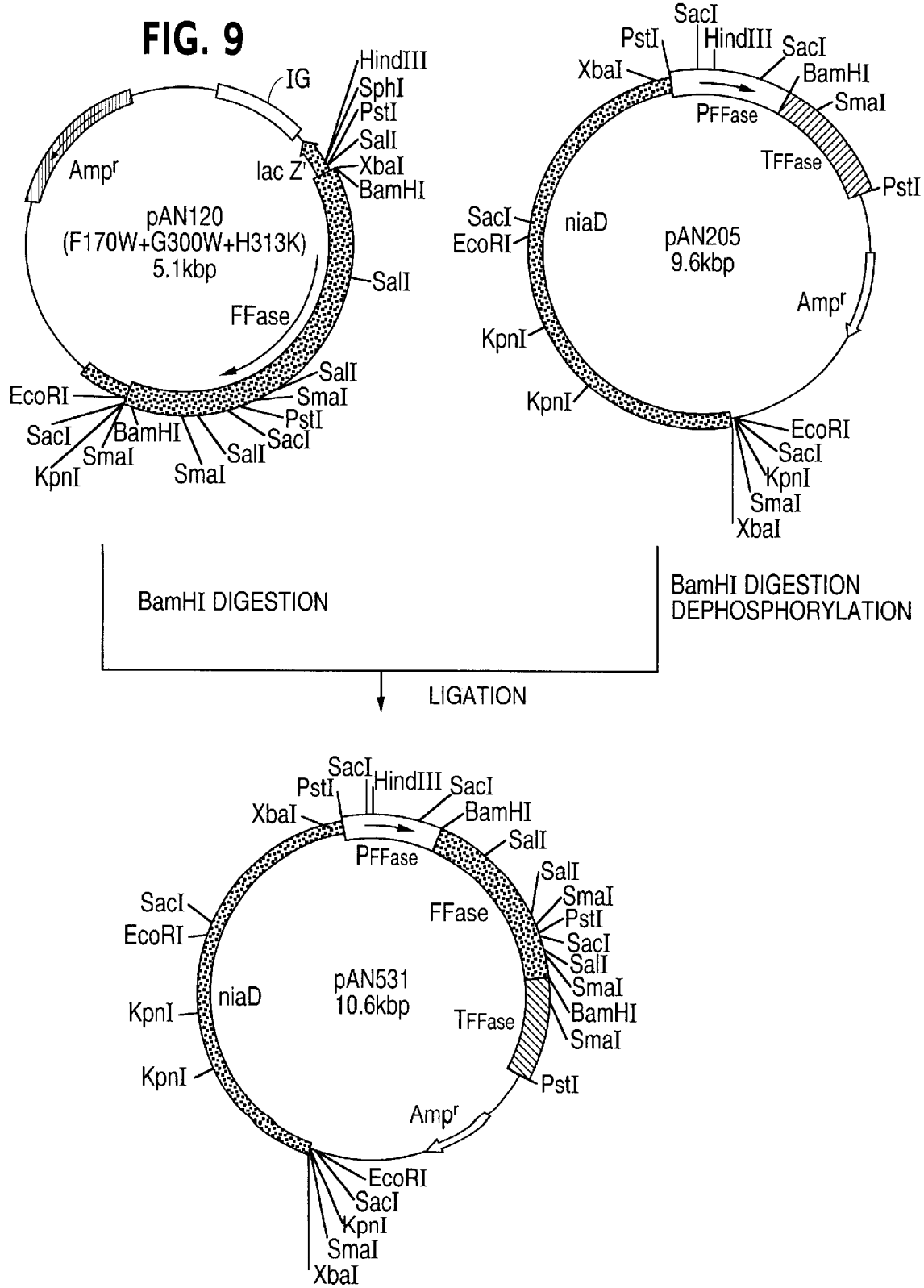
FIG. 9 shows the construction of plasmid pAN531.

(4) Production of variant F170W+G300W+H313K by *Aspergillus niger* and its evaluation A 2 kbp BamHI DNA fragment including the variant gene was prepared from plasmid pAN120 (F170W+G300W+H313K) by digesting it with BamHI, and inserted into the BamHI site of pAN205 (see Example C5) as shown in FIG. 9 (plasmid pAN531).

Plasmid pAN531 was digested with HindIII to linearize, then used to transform the *Aspergillus niger* NIA1602 (Suc⁻, niaD). The chromosomal DNA of the transformant was subjected to the Southern analysis, in order to select transformant in which only one copy of plasmid pAN531 was inserted at the location of β-fructofuranosidase gene on the host chromosome by homologous recombination in the promoter region of the β-fructofuranosidase gene.

Next, to delete the vector DNA from the transformant, conidia were prepared and applied to a medium containing chlorate (6% potassium chlorate, 3% sucrose, 0.2% sodium glutamate, 0.1% $K_2HPO_4$, 0.05% $MgSO_4.7H_2O$, 0.05% KCl, 0.01% $FeSO_4.7H_2O$ and 1.5% agar). It was assumed that a transformant which formed colonies on the medium had lost the vector DNA as a result of a secondary homologous recombination. If the secondary recombination took place in the same promoter region as in the first one, the transformant would change to the original host; it took place in the terminator region of the β-fructofuranosidase gene, the gene encoding the F170W+G300W+H313K variant would remain. These two types of recombinants would easily be distinguished by β-fructofuranosidase activity. In the experiment, the ratio between chlorate-resistant strains with β-fructofuranosidase activity and those without was 1:1. The result of Southern analysis for the chromosomal DNA extracted from one of the variants which exhibited β-fructofuranosidase activity, named *Aspergillus niger* NIA3144 (Suc⁺, niaD), confirmed that the vector DNA was missing and the gene encoding the F170W+G300W+H313K variant was inserted at the location of the β-fructofuranosidase gene on the host chromosome.

Next, the *Aspergillus niger* NIA3144 was cultivated in an enzyme production medium (5% sucrose, 0.7% malt extract, 1% polypepton, 0.5% carboxymethyl cellulose and 0.3% NaCl) at 28° C. for 3 days. After the mycelia were ultrasonically homogenized, the β-fructofuranosidase activity of the homogenate was measured. The activity was 25 units per 1 ml of culture solution. The homogenate was added to a 55 wt % sucrose solution, pH 7, at a rate of 2.5 units per 1 g of sucrose, and maintained at 40° C. for 20 hours. After the reaction, the sugar composition as measured by HPLC was 1.2% fructose, 22.8% glucose, 17.1% sucrose, 55.3% GF2 and 3.8% GF3.

(5) Preparation and enzymology of variant F170W+G300W+H313K

The homogenate prepared in (4) above was dialyzed with 20 mM Tris-HCl (pH 7.5) buffer solution, then subjected to a DEAE Toyopearl 650S (Tosoh) column (1.6×18 cm), which had been equalized with the same buffer solution, and eluted in Tris-HCl (pH 7.5) buffer solution with a linear gradient of 0 to 300 mM NaCl concentration. The collected active fraction was subjected to (applied to) a Sephacryl S-300 (Pharmacia) column (2.6×60 cm), and eluted in 50 mM trimethylamine-acetate buffer solution (pH 8.0). The collected active fraction was used as a purified F170W+G300W+H313K variant sample. As a result of SDS-polyacrylamide gel electrophoresis, the sample exhibited a single band at about 100,000 Da as did the original β-fructofuranosidase.

Further, the optimum pH, optimum temperature, stability to pH, and stability to temperature of the purified sample were almost the same as those of the original β-fructofuranosidase.

Example D12
Construction and Production of Variant F170W+G300V+H313K (1) Nucleotide substitution in β-fructofuranosidase gene by site-specific mutation Site specific mutations were induced in the same manner as in Example D1 except that the DNA primers of SEQ ID Nos. 28, 30 and 33 as shown in the sequence listing were used to construct plasmid pAN120 (F170W+G300V+H313K).

The result of sequencing for the inserted fragment of pAN120 (F170W+G300V+H313K) confirmed that substitution occurred only in the target nucleotides and no other part of the sequence. In other words, the β-fructofuranosidase encoded by the variant gene was the same as the original enzyme except that tryptophan was substituted for phenylalanine at position 170, valine for glycine at position 300, and lysine for histidine at position 313.

(2) Production of variant F170W+G300V+H313K by *Aspergllus niger* and its evaluation A 2 kbp BamHI DNA fragment including the variant gene was prepared from plasmid pAN120 (F170W+G300V+H313K) by digesting it with BamHI, and inserted into the BamHI site of pAN205 (plasmid pAN517).

Plasmid pAN517 was digested with HindIII to linearize, then used to transform the *Aspergillus niger* NIA1602 (Suc⁻, niaD) to prepare the *Aspergillus niger* NIA1717 (Suc⁺, niaD), in which the vector DNA was missing and the gene encoding the F170W+G300V+H313K variant was inserted at the location of the β-fructofuranosidase gene on the host chromosome, in the same manner as in Example D11.

Next, the *Aspergillus niger* NIA1717 was cultivated in an enzyme production medium (5% sucrose, 0.7% malt extract, 1% polypepton, 0.5% carboxymethyl cellulose and 0.3% NaCl) at 28° C. for 3 days. After the mycelia were ultrasonically homogenized, the β-fructofuranosidase activity of the homogenate was measured. The activity was 45 units per 1 ml of culture solution. The homogenate was added to a sucrose solution, Bx 45, pH 7.5, at a rate of 2.5 units per 1 g of sucrose, and maintained reaction at 40° C. for 24 hours. After the reaction, the sugar composition as measured by HPLC was 1.8% fructose, 22.3% glucose, 16.1% sucrose, 55.7% GF2 and 4.1% GF3. These figures indicate that GF2 increases and GF3 decreases as a result of the substitution in F170W+G300V+H313K.

(3) Preparation and enzymology of variant F170W+G300V+H313K

The homogenate prepared in (2) above was dialyzed with 20 mM Tris-HCl (pH 7.5) buffer solution, then subjected to (applied to) a DEAE Toyopearl 650S (Tosoh) column (1.6×

18 cm), which had been equalized with the same buffer solution, and eluted in Tris-HCl (pH 7.5) buffer solution with a linear gradient of 0 to 300 mM NaCl concentration. The collected active fraction was subjected to (applied to) a Sephacryl S-300 (Pharmacia) column (2.6×60 cm), and eluted in 50 mM trimethylamine-acetate buffer solution (pH 8.0). The collected active fraction was used as a purified F170W+G300V+H313K variant sample. As a result of SDS-polyacrylamide gel electrophoresis, the sample exhibited a single band at about 100,000 Da as did the original β-fructofuranosidase.

Further, the optimum pH, optimum temperature, stability to pH, and stability to temperature of the purified sample were almost the same as those of the original β-fructofuranosidase.

What is claimed is:

1. An isolated polypeptide comprising the amino acid sequence of SEQ ID No. 1 or a variant thereof, said polypeptide and said variant having β-fructofuranosidase activity, and said variant comprising an amino acid sequence of SEQ ID No. 1 substituted by other amino acids at one or more amino acid residues at the positions selected from the group consisting of positions 170, 300, 313, and 386 in the amino acid sequence of SEQ ID No. 1.

2. The polypeptide according to claim 1, which improves the selectivity and/or efficiency of 1-kestose.

3. The polypeptide according to claim 1, wherein said variant comprises an amino acid sequence of SEQ ID No. 1 in which the amino acid residue at position 170 of SEQ ID No. 1 is substituted by an aromatic amino acid selected from the group consisting of tryptophan, phenylalanine and tyrosine.

4. The polypeptide according to claim 1, wherein said variant comprises an amino acid sequence of SEQ ID No. 1 in which the amino acid residue at position 300 of SEQ ID No. 1 is substituted by an amino acid selected from the group consisting of tryptophan, valine, glutamic acid and aspartic acid.

5. The polypeptide according to claim 1, wherein said variant comprises an amino acid sequence of SEQ ID No. 1 in which the amino acid residue at position 313 of SEQ ID No. 1 is substituted by a basic amino acid selected from the group consisting of lysine, arginine and histidine.

6. The polypeptide according to claim 1, wherein said variant comprises an amino acid sequence of SEQ ID No. 1 in which the amino acid residue at position 386 of SEQ ID No. 1 is substituted by a basic amino acid selected from the group consisting of lysine, arginine and histidine.

7. The polypeptide according to claim 1, wherein said variant comprises an amino acid sequence of SEQ ID No. 1 in which the amino acid residues at positions 170, 300 and 313 of SEQ ID No. 1 are substituted by tryptophan, tryptophan and lysine, respectively.

8. The polypeptide according to claim 1, wherein said variant comprises an amino acid sequence of SEQ ID No. 1 in which the amino acid residues at positions 170, 300 and 313 of SEQ ID No. 1 are substituted by tryptophan, valine and lysine, respectively.

9. An isolated polypeptide comprising the amino acid sequence of SEQ ID No. 11, said polypeptide having β-fructofuranosidase activity.

10. An isolated polypeptide comprising the amino acid sequence of SEQ ID No. 13, said polypeptide having β-fructofuranosidase activity.

* * * * *